United States Patent [19]

Naruto et al.

[11] Patent Number: 5,643,925
[45] Date of Patent: Jul. 1, 1997

[54] BENZENE DERIVATIVES HAVING NGF PRODUCTION-PROMOTING ACTIVITY

[75] Inventors: Shunji Naruto; Yuichi Sugano; Keiichi Matsuda; Masahiko Sugimoto; Tomiichiro Oda, all of Tokyo, Japan

[73] Assignee: Sankyo Company, Limited, Tokyo, Japan

[21] Appl. No.: 837,491

[22] Filed: Feb. 18, 1992

[30] Foreign Application Priority Data

Feb. 21, 1991 [JP] Japan .................................. 3-027060

[51] Int. Cl.$^6$ ..................... A01N 43/42; C07D 215/38; C07D 215/14
[52] U.S. Cl. ..................... 514/311; 546/162; 546/171; 514/313
[58] Field of Search ..................... 544/168; 514/311, 514/313, 231.2, 330; 546/171, 162, 189

[56] References Cited

U.S. PATENT DOCUMENTS 3,147,261 9/1964 Mod et al. .............................. 546/168
3,539,578 11/1970 Brown .................................. 546/168

FOREIGN PATENT DOCUMENTS 0 172 631  2/1986  European Pat. Off. .
0 333 522  9/1989  European Pat. Off. .
0 399 814  11/1990 European Pat. Off. .
3-83921    4/1991  Japan .

OTHER PUBLICATIONS

Chemical Abstracts vol. 112, No. 138,764, Fukazawa et al, Sep. 20, 1989, "Preparation of Catechol Derivatives for Use in Disorder of Central Nervous Treatment".
*Chemical Abstracts*, vol. 115, No. 270827 (1991).
Lenz et al., *Biol. Chem. Hoppe-Seyler*, 372, 495–504, Jul. 1991.

Chemical Abstracts, vol. 105, No. 13, 29 Sep. 1986, Columbus, Ohio, US; Abstract No. 115063b, M.H. Hockley, R.B. Titman "Therapeutic agents" of EP-A-0 172 631.
Patent Abstracts of Japan, vol. 14, No. 310 (C-736) (4253), 4 Jul. 1990 of JP-A-02 104 568.

*Primary Examiner*—Bernard Dentz
*Assistant Examiner*—Raymond Covington
*Attorney, Agent, or Firm*—Frishauf, Holtz, Goodman, Langer & Chick, P.C.

[57] ABSTRACT

Novel benzene derivatives are provided of the general formula (I):

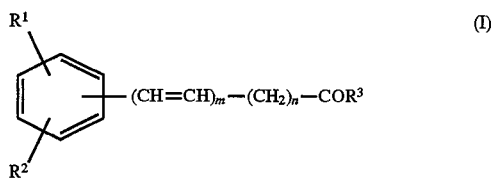

[wherein $R^1$ represents an amino group, a substituted amino group, a protected amino group, or a nitro group; $R^2$ represents an amino group, a substituted amino group, a protected amino group, a hydroxy group, a substituted hydroxy group, or a protected hydroxy group; $R^3$ represents an amino group, a substituted amino, a heterocyclyl group having a ring nitrogen atom as the point of binding, or a substituted heterocyclyl group having a ring nitrogen atom as the point of binding; m is 0 to 2; n is 0 to 6; with the proviso that when m is 0, then n represents an integer from 2 to 6] and salts thereof.

Compounds of formula (I) except those wherein $R^1$ is a nitro group have activity in promoting production of nerve growth factor. Compounds of formula (I) wherein $R^1$ is a nitro group are intermediates for compounds of formula (I) wherein $R^1$ is an amino group.

13 Claims, No Drawings

BENZENE DERIVATIVES HAVING NGF PRODUCTION-PROMOTING ACTIVITY

BACKGROUND OF THE INVENTION

The present invention relates to novel benzene derivatives which promote production or secretion of nerve growth factor (abbreviated to "NGF"), while exhibiting weak side effects.

The discovery of NGF was reported by Levi-Montaleini et al. in 1954. NGF is a nutrient and growth factor necessary for growth and for functional maintenance of nerve tissues. Recently from studies on animals, it has become known that NGF accelerates restoration of injured peripheral nerve tissue and that NGF is effective in the therapy of central nervous dysfunction, especially Alzheimer's disease and cerebral ischemia.

However, NGF is a high molecular weight protein (having a molecular weight of 13000 for the monomeric form, and 26000 for the dimeric form), and so there are problems associated with its administration as a drug and general concerns for safety.

It is also known that catechol neurotransmitters such as adrenaline and noradrenaline, and catechol analogs, can promote NGF formation. These compounds have side effects, particularly in nerve excitation.

European Patent Specification 399,814 published on 28 November 1990 discloses phenol derivatives which promote the production and secretion of human nerve growth factor. Related compounds of similar utility are disclosed in Japanese Patent Application 1-217211 which was filed on 25 August 1989 and published as Japanese Patent Kokai 3-83921 on 09 April 1991.

OBJECTS OF THE INVENTION

An object of the present invention is the development of benzene derivatives effective as drugs which promote nerve growth factor or effective as intermediates for the preparation of such drugs. A particular object is the provision of such drugs with reduced side effects, in particular with low nerve excitation activity. Further objects of this invention include the provision of pharmaceutical compositions for use in treatment of peripheral nerve damage and treatment of damage to the functioning of the central nervous system, especially in Alzheimer's disease and brain ischemia.

SUMMARY OF THE INVENTION

In accordance with the present invention, there are provided novel benzene derivatives of the general formula (I):

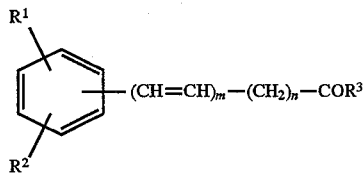

wherein:

$R^1$ represents an amino group, a substituted amino group substituted by 1 or 2 groups selected from the members of Substituent Group A, a protected amino group, or a nitro group;

$R^2$ represents an amino group, a substituted amino group substituted by 1 or 2 groups selected from the members of Substituent Group A, a protected amino group, a hydroxy group, a substituted hydroxy group substituted by a group selected from the members of Substitutent Group A, or a protected hydroxy group;

$R^3$ represents an amino group, a substituted amino group substituted by 1 or 2 groups selected from the members of Substituent Group A, a heterocyclyl group having a ring nitrogen atom as the point of binding, or a substituted heterocyclyl group having a ring nitrogen atom as the point of binding and substituted by 1 or 2 groups selected from the members of Substituent Group A and Substituent Group B;

m represents an integer from 0 to 2;

n represents an integer from 0 to 6;

Substituent Group A consists of the following members: alkyl groups, haloalkyl groups containing 1 to 3 halogen atoms, cycloalkyl groups, substituted cycloalkyl groups substituted by 1 to 3 groups selected from the members of Substituent Group B and Substituent Group C, aryl groups, substituted aryl groups substituted by 1 to 3 groups selected from the members of Substituent Group B and Substituent Group C, aralkyl groups, substituted aralkyl groups substituted on at least 1 aryl ring by 1 to 3 groups selected from the members of Substituent Group B and Substituent Group C, heterocyclyl groups, and substituted heterocyclyl groups substituted by 1 to 3 groups selected from the members of Substituent Group B and Substituent Group C;

Substituent Group B consists of the following members: halogen atoms, alkoxy groups, alkoxycarbonyl groups, a nitro group, a cyano group, arylcarbonyl and aralkylcarbonyl groups; and Substituent Group C consists of the following members: alkyl groups, haloalkyl groups containing 1 to 3 halogen atoms, and cycloalkyl groups;

with the proviso that when m is 0, then n represents an integer from 2 to 6;

and salts thereof.

Compounds of formula (I) wherein $R^1$ is a nitro group are intermediates for compounds of formula (I) wherein $R^1$ is an amino group.

PREFERRED EMBODIMENTS OF THE INVENTION

Alkyl groups in the definition of the compounds of the present invention typically comprise straight or branched chain alkyl groups having from 1 to 6 carbon atoms, for example a methyl, ethyl, propyl, isopropyl, butyl, isobutyl, sec-butyl, tert-butyl, pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. Preferred alkyl groups are straight or branched chain alkyl groups having from 1 to 4 carbon atoms.

Cycloalkyl groups in the definition of the compounds of the present invention typically comprise 3- to 10-membered saturated cyclic hydrocarbon groups which may optionally be bridged, for example a cyclopropyl, cyclobutyl, cyclopentyl, cyclohexyl, cycloheptyl, norbornyl or adamantyl group. Preferred cycloalkyl groups are 5- to 10-membered opitionally bridged saturated cyclic hydrocarbon groups. A particularly preferred cycloalkyl group is an adamantyl group.

Aryl groups in the definition of the compounds of the present invention typically comprise 6- to 14-membered aromatic cyclic hydrocarbon groups, for example a phenyl, naphthyl, phenanthrenyl or anthracenyl group; preferably a phenyl group. The aryl group may be fused with a 3- to 10-membered cycloalkyl group, giving for example a 2-indanyl group.

Aralkyl groups in the definition of the compounds of the present invention typically comprise 1 alkyl group substituted by 1 to 3 aryl groups. Examples of such aralkyl groups include a benzyl, naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl or 6-naphthylhexyl group. Preferred-aralkyl groups have from 1 to 4 carbon atoms in the alkyl group part. A particularly preferred aralkyl group is a benzyl group.

Heterocyclyl groups in the definition of the compounds of the present invention generally comprise an optionally fused 5- to 7-membered heterocyclyl group containing from 1 to 4 heteroatoms selected from nitrogen atoms, oxygen atoms and sulfur atoms. This generality is subject where indicated to the requirement specified that certain heterocyclyl groups have a ring nitrogen atom as their point of binding: such heterocyclyl groups may have more than one nitrogen heteroatom. The heterocyclyl group can be aromatic or partly or fully saturated, and can be fused with 1 or 2 aryl rings, usually with 1 or 2 benzene rings.

Typical heterocyclyl groups embracing heterocyclyl groups in general and also embracing heterocyclyl groups having a ring nitrogen atom as their binding point comprise:

aromatic heterocyclyl groups, for example a furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl or pirazinyl group;

partially or completely reduced heterocyclyl groups, for example a morpholinyl, thiomorpholinyl, pyrrolidinyl, pyrrolinyl, imidazolidinyl, imidazolinyl, pyrazolidinyl, pyrazolinyl, piperidyl or piperazinyl group;

fused aromatic heterocyclic groups, for example a isobenzofuranyl, benzothienyl, tetrahydrobenzothienyl, chromenyl, xanthenyl, phenoxathienyl, indolidinyl, isoindolyl, indolyl, indazolyl, purinyl, quinolidinyl, isoquinolyl, quinolyl, phthalazinyl, naphthyridinyl, quinoxalinyl, quinazolinyl, carbazolyl, carbolinyl, acridinyl or isoindolinyl group; or partially or completely saturated fused heterocyclyl groups, for example a tetrahydrobenzothienyl group.

Preferred heterocyclyl groups are 5- to 7-membered heterocyclic groups containing at least one nitrogen atom and further optionally containing 1 sulfur or oxygen atom, which may optionally be partially or completely saturated and may optionally be fused to an aryl ring. Such preferred heterocycle groups include:

aromatic heterocyclic groups, for example a pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl or pirazinyl group;

partially or completely saturated heterocyclyl group, for example a morpholinyl, thiomorpholinyl, pyrrolidinyl, pyrrolinyl, imidazolidinyl, imidazolinyl, pyrazolidinyl, pyrazolinyl, piperidyl or piperazinyl group; or fused heterocyclyl groups, for example a quinolyl or benzothienyl group.

Particularly preferred heterocycle groups comprise an imidazolyl, oxazolyl, isoxazolyl, thiazolyl, piperidyl or piperazyl group.

Halogen atoms in the definition of the compounds of the present invention can suitably be a fluorine, chlorine, bromine or iodine atom.

Alkoxy groups in the definition of the compounds of the present invention typically comprise a said alkyl group and an oxygen atom, giving straight or branched chain alkoxy groups having from 1 to 6 carbon atoms, for example a methoxy, ethoxy, propoxy, isopropoxy, butoxy, isobutoxy, sec-butoxy, tert-butoxy, pentoxy, isopentoxy, 2-methylbutoxy, neopentoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group Preferred alkoxy groups are straight or branched chain alkoxy groups having from 1 to 4 carbon atoms.

Haloalkyl groups in the definition of the compounds of the present invention typically comprise a said alkyl group and 1 to 3 halogen atoms, for example a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl or 2,2-dibromoethyl group. A preferred haloalkyl group is a halogenomethyl group. A particularly preferred haloalkyl group is a trifluoromethyl group.

The protected amino groups which may be adopted for the group $R^1$ and/or for the group $R^2$ comprise an amino group protected by 1 or 2 amino protecting groups. The identity of the protecting group is not particularly critical, and typically it is one conventionally used for protection of an amino group, preferably for instance:

aliphatic acyl groups such as an alkanoyl group having from 1 to 20 carbon atoms, for example a formyl, acetyl, propionyl, butyryl, isobutyryl, pentanoyl, pivaloyl, valeryl, isovaleryl, octanoyl, lauroyl, myristoyl, tridecanoyl, palmitoyl or stearoyl group, such as a halogenated aliphatic acyl group, more especially a haloalkanoyl group having from 1 to 6 carbon atoms and having from 1 to 3 halogen atoms, for example a chloroacetyl, dichloroacetyl, trichloroacetyl or trifluoroacetyl group, such as an alkoxy aliphatic acyl group, more especially an alkoxyalkanoyl group having from 1 to 6 carbon atoms in the alkoxy group and 1 to 6 carbon atoms in the alkanoyl group, for example a methoxyacetyl group, or such as an unsaturated aliphatic acyl group, more especially an alkenoyl group having from 1 to 6 carbon atoms, for example an (E)-2-methyl-2-butenoyl group; an aromatic acyl group such as an arylcarbonyl group, for example a benzoyl, α-naphthoyl or β-naphthoyl group, such as a haloarylcarbonyl group, more especially a haloarylcarbonyl group having from 1 to 3 halogen substituents, for example a 2-bromobenzoyl or 4-chlorobenzoyl group, such as an alkylarylcarbonyl group, more especially an alkylarylcarbonyl group having from 1 to 3 alkyl substituents each having from 1 to 3 carbon atoms, for example a 2,4,5-trimethylbenzoyl or 4-toluoylgroup, such as an alkoxyarylcarbonyl group, more especially an alkoxyarylcarbonyl group having from 1 to 3 alkoxy substituents each having from 1 to 3 carbon atoms, for example a 4-anisoyl group, such as a nitroarylcarbonyl group, more especially a nitroarylcarbonyl group having 1 or 2 nitro substituents, for example a 4-nitrobenzoyl or 2-nitrobenzoyl group, such as an alkoxycarbonylarylcarbonyl group, more especially an alkoxycarbonylarylcarbonyl group having 1 or 2 alkoxycarbonyl substituents each having from 1 to 3 carbon atoms in the alkoxy group, for example a 2-(methoxycarbonyl) benzoyl group, such as an arylarylcarbonyl group, for example a 4-phenylbenzoyl group;

alkoxycarbonyl groups such as an alkoxycarbonyl group comprising a said alkoxy group and a carbonyl group, giving straight or branched chain alkoxycarbonyl groups having from 2 to 7 carbon atoms, for example a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, isopentoxycarbonyl, 2-methylbutoxycarbonyl, neopentoxycarbonyl, hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl or 2,3-dimethylbutoxycarbonyl group, preferably a straight or branched chain alkoxycarbonyl group having from 2 to 5 carbon atoms, such as a haloalkoxycarbonyl group, more especially a haloalkoxy group of which the alkoxy group has 1 to 6 carbon atoms and has from 1 to 3 halogen substituents, for example a 2,2,2-trichloroethoxycarbonyl group, or such as an trialkylsilylalkoxy group, more especially a trialkylsilylalkoxy group having 1 to 6 carbon atoms in each alkyl group and having 1 to 6 carbon atoms in the alkoxy group, for example a 2-trimethylsilylethoxycarbonyl group;

alkenyloxycarbonyl groups, more especially an alkenyloxycarbonyl group having 1 to 6 carbon atoms in the alkenyl group, for example a vinyloxycarbonyl or allyloxycarbonyl group; an optionally substituted aralkyloxycarbonyl group, more especially an aralkyloxycarbonyl group in which the aryl ring is optionally substituted by 1 to 3 alkoxy groups having 1 to 6 carbon atoms or by 1 or 2 nitro groups, for example a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group group;

silyl groups such as a tri-alkylsilyl group having 1 to 6 carbon atoms in each alkyl group, for example a trimethylsilyl, triethylsilyl, isopropyldimethylsilyl, tert-butyldimethylsilyl, methyldiisopropylsilyl, methyl-di-tert-butylsilyl or triisopropylsilyl group, or such as a mixed alkyl/aryl tri-substituted-silyl group with 1 or 2 alkyl groups each having 1 to 6 carbon atoms and correspondingly having 2 or 1 aryl groups, for example a diphenylmethylsilyl, diphenylbutylsilyl, diphenylisopropylsilyl or phenyldiisopropylsilyl group;

amino acid residues, for example an alanyl, glycyl, glutamyl or asparaginyl group;

substituted methylene groups forming a Schiff base, for example an N,N-dimethylaminomethylene, benzylidene, 4-methoxybenzylidene, 4-nitrobenzylidene, salicylidene, 5-chlorosalicylidene, diphenylmethylene or (5-chloro-2-hydroxyphenyl)phenylmethylene group.

Of these preferred protecting groups for amino groups, the more preferred protecting groups comprise an aliphatic acyl or aromatic acyl group or an amino acid residue.

The protected hydroxy group which may be adopted for the group $R^2$ may be a hydroxy protecting group effective as a protecting group in a chemical reaction, or by a hydroxy protecting group hydrolyzable in vivo upon administration. In the former case, the compounds of formula (I) are synthetic intermediates. In the latter case, the compounds of formula (I) are pro-drugs. The identity of the protecting group is not particularly critical, and typically it is one conventionally used for protection of a hydroxy group, preferably for instance:

for a synthetic intermediate:

a said aliphatic acyl group; a said aromatic acyl group; a tetrahydropyranyl or tetrahydrothiopyranyl group optionally substituted by 1 or 2 alkoxy groups having 1 to 6 carbon atoms or by 1 or 2 halogen atoms, for example a tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl group; a tetrahydrofuranyl or tetrahydrothiofuranyl group, for example a tetrahydrofuran-2-yl or tetrahydrothiofuran-2-yl group; a said silyl group; an alkoxymethyl group such as an alkoxymethyl group having 1 to 6 carbon atoms in the alkoxy group, for example a methoxymethyl, 1,1-dimethyl-1-methoxymethyl, ethoxymethyl, propoxymethyl, isopropoxymethyl, butoxymethyl or tert-butoxymethyl group, such as an alkoxyalkoxymethyl group, more especially an alkoxyalkoxymethyl group having 1 to 6 carbon atoms in each alkoxy group, for example a 2-methoxyethoxymethyl group, or such as a haloalkoxymethyl group, more especially a mono- or di-(haloalkoxy) methyl group having 1 to 6 carbon atoms in the alkoxy group and having 1 to 3 halogen substituents, for example a 2,2,2-trichloroethoxymethyl or bis(2-chloroethoxy)methyl group; a substituted ethyl group, more especially an alkoxyor haloalkoxyethyl group having 1 to 6 carbon atoms in the alkoxy group and having 0 to 3 halogen substituents, for example a 1-ethoxyethyl or 1-(isopropoxy) ethyl group, or for example a 2,2,2-trichloroethyl group; a said alkoxycarbonyl group; a said alkenyloxycarbonyl group; or a said aralkyloxycarbonyl group; or for a pro-drug:

an amino acid residue, for example an alanyl, glycyl, glutamyl or asparaginyl group; or such as a pivaloyloxymethyloxycarbonyl group.

Of these preferred protecting groups for hydroxy groups, the more preferred protecting groups comprise an aliphatic acyl group, an aromatic acyl group, an aralkyl group, or a protecting group which is easily hydrolyzed in vivo and employed for preparing a pro-drug for administration.

In the definition of the group $R^3$, the heterocyclyl group binding at the nitrogen atom on its ring, which can be a substituted heterocyclyl group substituted as defined, is suitably an optionally fused 5- to 7-membered heterocyclyl group containing the binding nitrogen atom and optionally further containing from 1 or 2 further heteroatoms selected from nitrogen atoms, oxygen atoms and sulfur atoms. This heterocyclyl group can be aromatic or partly or fully saturated, and can be fused with 1 or 2 aryl rings, usually with 1 or 2 benzene rings.

Preferred heterocyclyl groups include an aromatic heterocyclyl group, for example a pyrrolyl, azepinyl, pyrazolyl, imidazolyl, oxazolyl, isoxazolyl, thiazolyl, isothiazolyl, 1,2, 3-oxadiazolyl, triazolyl, tetrazolyl, thiadiazolyl, pyridyl, pyridazinyl, pyrimidinyl or pyrazinyl group; a partially or completely saturated heterocyclyl group, for example a morpholinyl, thiomorpholinyl, pyrrolidinyl, pyrrolinyl, imidazolidinyl, imidazolinyl, pyrazolidinyl, pyrazolinyl, piperidyl or piperazinyl; more preferably a morpholinyl, thiomorpholinyl, piperidyl or piperazyl group; or a condensed heterocyclyl group, for example an indolidinyl, isoindolyl, indolyl, indazolyl, purinyl, quinolidinyl, isoquinolyl, quinolyl, phthalazinyl, naphthyridinyl, quinoxalinyl, quinazolinyl, carbazolyl, carbolinyl or acridinyl group.

Preferred examples of a substituted amino group substituted by 1 to 2 groups selected from the members of Substituent Group A comprise an amino group substituted by 1 or 2 straight or branched chain alkyl groups having from 1 to 4 carbon atoms, such as a methylamino, ethylamino, propylamino, isopropylamino, butylamino, isobutylamino, dimethylamino, diethylamino or methylethylamino group; an amino group substituted by one straight or branched chain alkyl group having from 1 to 4 carbon atoms and one 6- to 10-membered aromatic cyclic hydrocarbon group such as methylphenylamino, ethylphenylamino, propylphenylamino, isopropylphenylamino, butylphenylamino, isobutylphenylamino; an amino group substituted by one or two 5- to 10-membered optionally bridged saturated cyclic hydrocarbon groups such as a cyclopentylamino, cyclohexylamino or 1-adamantylamino group; an amino group substituted by one or two 6- to 10-membered aromatic cyclic hydrocarbon groups optionally fused with a cycloalkyl group and optionally substituted by 1 or 2 groups selected from the members of Substituent Group B and Substituent Group C, such as an arylamino group, for example a phenylamino, diphenylamino, 1-indanylamino or naphthylamino group, a haloarylamino group, for example a 2-fluorophenylamino, 3-bromophenylamino, 4-fluoro-phenylamino, 2-fluoroindan-1-ylamino, 3,4-difluoro-phenylamino, 2,4-difluorophenylamino, 2,5-difluoro-phenylamino, 2-chlorophenylamino, 3-chlorophenylamino, 4-chlorophenylamino, 3,4-dichlorophenylamino, 2,4-dichlorophenylamino, 2,5-dichlorophenylamino or 2-fluoronaphthylamino group, a $C_{1-4}$-alkoxy-arylamino group, for example a 2-ethoxyphenylamino, 3-propoxyphenylamino, 4-methoxyphenylamino, 3,4-dimethoxyphenylamino, 2,4-dimethoxyphenylamino, 2,5-dimethoxyphenylamino or 2-methoxynaphthylamino group, a nitroarylamino group, for example a 2-nitrophenylamino, 3-nitrophenylamino or 4-nitrophenylamino group, a cyanoarylamino group, for example a 2-cyanophenylamino, 3-cyanophenylamino or 4-cyanophenylamino group, a benzoylarylamino group, for example a 2-benzoylphenylamino, 3-benzoylphenylamino, 4-benzoylphenylamino or 2-benzoylnaphthylamino group, a halo-$C_{1-4}$-alkyl-arylamino group, for example a 2-trifluoromethylphenylamino, 3-trichloromethylphenylamino, 4-trifluoromethylphenylamino, 2,4-ditrifluoromethylphenylamino or 2,5-ditrifluoromethylphenylamino group, a $C_{1-4}$-alkyl-arylamino group, for example a 2-methylphenylamino, 3-methylphenylamino, 4-methylphenylamino, 3,4-dimethylphenylamino, 2,4-dimethylphenylamino, 2,5-dimethylphenylamino, 2-ethylphenylamino, 3-propylphenylamino, 4-butylphenylamino, 3,4-diethylphenylamino, 2,4-diethylphenylamino, 2,5-dipropylphenylamino, 3,4,5-trimethylphenylamino or 2-methylnaphthylamino group; an amino group substituted by 1 or 2 heterocyclyl groups, such as a tetrahydrobenzothiophen-2-yl amino, quinolin-2-yl amino, quinolin-3-ylamino, quinolin-5-ylamino, quinolin-8-ylamino, pyridin-2-ylamino, pyridin-3-ylamino, pyridin-4-ylamino, morpholin-2-ylamino, morpholin-3-ylamino, piperidin-2-ylamino, piperidin-3-ylamino, piperidin-4-ylamino, piperazin-2-ylamino or piperazin-3-ylamino group; an amino group substituted by 1 or 2 heterocyclyl groups substituted by 1 or 2 groups selected from the members of Substituent Group B and Substituent Group C, such as a haloheterocyclylamino group, for example a 3-fluorotetrahydrobenzothiophen-2-ylamino, 3-bromopiperidin-4-ylamino, 2-fluoroquinolin-3-ylamino, 3-fluoromorpholin-2-ylamino, 3-fluoropiperazin-2-ylamino, 2-chloropiperidin-4-yl-amino, 3-chlorotetrahydrobenzothiophen-2-ylamino, 4-chloropiperidin-2-ylamino or 2,6-dichloropiperidin-4-ylamino group, a $C_{1-4}$-alkoxyheterocyclylamino group, for example a 3-ethoxymorpholin-2-ylamino, 4-methoxyquinolin-5-ylamino or 2,6-dimethoxypiperidin-4-ylamino group, a $C_{2-5}$-alkoxycarbonyl- heterocyclylamino group, for example a 3-methoxycarbonyltetrahydrobenzothiophen-2-ylamino or 4-ethoxycarbonyltetrahydrobenzothiophen-2-ylamino group, a cyanoheterocyclylamino group, for example a 3-cyanopyridin-2-ylamino, 3-cyanotetrahydrobenzothiophen-2-yl- amino or 3-cyanopiperazin-2-ylamino group, a halo-$C_{1-4}$-alkylheterocyclylamino group, for example a 2-trifluoromethylquinolin-3-ylamino, 3-trichloromethylmethylmorpholin-2-ylamino, 4-trifluoromethyltetrahydrobenzothiophen-2-ylamino or 2,6-ditrifluoromethylpiperidin-4-ylamino group, or a $C_{1-4}$-alkyl-heterocyclylamino group, for example a 3-methyltetrahydrobenzothiophen-2-ylamino, 4-methyltetrahydrobenzothiophen-2-ylamino, 4-methylpiperidin-2-ylamino, 2,6-dimethylpyridin-4-ylamino or 2,5-dimethylpyridin-4-ylamino group.

Preferred examples of a substituted hydroxy group substituted by a group selected from the members of Substituent Group A comprise a hydroxy group substituted by a straight or branched chain alkyl group having from 1 to 4 carbon atoms, giving a straight or branched chain alkoxy group having from 1 to 4 carbon atoms, such as a methoxy, ethoxy, propoxy, isopropoxy, butoxy or isobutoxy group; a hydroxy group substituted by an aralkyl group, giving an aralkoxy group, such as a benzyloxy, phenethyloxy or diphenylmethyloxy group.

Preferred examples of a substituted heterocyclyl group having a ring nitrogen atom as the point of binding and substituted by 1 to 2 groups selected from the members of Substituent Group A and Substituent Group B comprise a halo 5- or 6-membered heterocyclyl group such as a 3-bromopiperidino, 3-fluoromorpholinyo, 2-fluoropiperazino, 2-chloropiperidino, 4-chloropiperidino or 2,4-dichloropiperidino group; a $C_{1-4}$-alkoxy 5- or 6-membered heterocyclyl group such as a 2-ethoxymorpholino or 3,4-dimethoxypiperidino group; a $C_{2-5}$-alkoxycarbonyl 5- or 6-membered heterocyclyl group such as a 2-methoxycarbonylmorpholino or 2-methoxycarbonylpiperazino group; a nitro 5- or 6-membered heterocyclyl group such as a 3-nitropiperidino group; a cyano 5- or 6-membered heterocyclyl group such as a 4-cyanopiperidino or 3-cyanopiperazino group; a benzoyl 5- or 6-membered heterocyclyl group such as a 2-benzoylpiperidino group; a halo-$C_{1-4}$-alkyl- 5- or 6-membered heterocyclyl group such as a 3-trichloromethylmorpholino or 2,5-ditrifluoromethylpiperidino; a $C_{1-4}$ alkyl 5- or 6-membered heterocyclyl group such as a 4-methylpiperidino, 2-ethylpiperidino or 3-pyrrolidino group; or a $C_{5-10}$-cycloalkyl- 5- or 6-membered heterocyclyl group such as a 4-cyclohexylpiperidino group.

Preferred examples of a substituted $C_{5-10}$-cycloalkyl group substituted by 1 to 3 groups selected from the members of Substituent Group B and Substituent Group C comprise: a halo-$C_{5-10}$-cycloalkyl group such as a 2-chlorocyclopentyl, 3-chlorocyclopentyl, 2-fluorocyclopentyl, 3-fluorocyclopentyl, 2-chlorocyclohexyl, 3-fluorocyclohexyl, 4-bromocyclohexyl, 3,4-difluorocyclohexyl, 2-fluoroadamantyl or 3-fluoroadamantyl group; a $C_{1-4}$-alkoxy- $C_{5-10}$-cycloalkyl group such as a 2-methoxycyclopentyl, 3-ethoxycyclopentyl, 2-propoxycyclohexyl, 3-methoxycyclohexyl, 4-methoxycyclohexyl, 2-methoxyadamantyl or 3-ethoxyadamantyl group; a $C_{2-5}$-alkoxycarbonyl- $C_{5-10}$ cycloalkyl group such as a 2-methoxycarbonylcyclopentyl, 3-ethoxycarbonylcyclopentyl, 2-methoxycarbonylcyclohexyl, 3-methoxycarbonylcyclohexyl, 4-ethoxycarbonylcyclohexyl, 2-propoxycarbonyladamantyl or 4-methoxycarbonyladamantyl group; a nitro- $C_{5-10}$-cycloalkyl group such as a 2-nitrocyclopentyl, 3-nitrocyclopentyl, 2-nitrocyclohexyl, 3-nitrocyclohexyl, 4-nitrocyclohexyl, 2-nitroadamantyl or 3-nitroadamantyl group; a cyano-$C_{5-10}$-cycloalkyl group such as a 2-cyanocyclopentyl, 3-cyanocyclopentyl, 2-cyanocyclohexyl, 3-cyanocyclohexyl, 4-cyanocyclohexyl, 2-cyanoadamantyl or 4-cyanoadamantyl group; a benzoyl-$C_{5-10}$-cycloalkyl group such as a 3-benzoylcyclopentyl, 3-benzoylcyclohexyl, 4-benzoylcyclohexyl or 2-benzoyladamantyl group; a halo- $C_{1-4}$-alkyl- $C_{5-10}$-cycloalkyl group such as a 3-trifluoroethylcyclopentyl, 4-trichloromethylcyclohexyl, 2-trifluoromethyladamantyl or 3-trifluoromethyladamantyl group; a $C_{1-4}$-alkyl-$C_{5-10}$ cycloalkyl group such as a 2-methylcyclopentyl, 3-ethylcyclopentyl, 2-methylcyclohexyl, 3-methylcyclohexyl, 4-propylcyclohexyl, 2-methyladamantyl or 3-methyladamantyl group; or a $C_{5-10}$-cycloalkyl-$C_{5-10}$-cycloalkyl group such as a 3-cyclohexylcyclopentyl or 4-cyclohexylcyclohexyl group.

Preferred examples of a substituted aryl group substituted by 1 to 3 groups selected from the members of Substituent Group B and Substituent Group C comprise a halo- $C_{6-10}$-aryl group such as a 2-fluorophenyl, 3-bromophenyl, 4-fluorophenyl, 3,4-difluorophenyl, 2,4-difluorophenyl, 2,5-difluorophenyl, 2-chlorophenyl, 3-chlorophenyl, 4-chlorophenyl, 3,4-dichlorophenyl, 2,4-dichlorophenyl, 2,5-dichlorophenyl, 3,4,5-tribromophenyl or 2-fluoronaphthyl group; a $C_{1-4}$-alkoxyl-$C_{6-10}$-aryl group such as a 2-ethoxyphenyl, 3-propoxyphenyl, 4-methoxyphenyl, 3,4-dimethoxyphenyl, 2,4-dimethoxyphenyl, 2,5-dimethoxyphenyl, 3,4,5-trimethoxyphenyl or 2-methoxynaphthyl group; a $C_{2-5}$-alkoxycarbonyl- $C_{6-10}$-aryl group such as a 2-methoxycarbonylphenyl, 4-ethoxycarbonylphenyl, 2-methoxycarbonylnaphthyl group; a nitro- $C_{6-10}$ aryl group such as a 2-nitrophenyl, 3-nitrophenyl, 4-nitrophenyl group; a cyano- $C_{6-10}$-aryl group such as a 2-cyanophenyl, 3-cyanophenyl, 4-cyanophenyl group; a benzoyl- $C_{6-10}$-aryl group such as a 2-benzoylphenyl, 3-benzoylphenyl, 4-benzoylphenyl, 2-benzoylnaphthyl group; a halo- $C_{1-4}$-alkyl- $C_{6-10}$-aryl group such as a 2-trifluoromethylphenyl, 3-trichloromethylphenyl, 4-trifluoromethylphenyl, 2,4-ditrifluoromethylphenyl, 2,5-ditrifluoromethylphenyl, 3,4,5-tris(trifluoromethyl)phenyl or 2-trifluoromethylnaphthyl group; a $C_{1-4}$ alkyl- $C_{6-10}$-aryl group such as a 2-methylphenyl, 3-methylphenyl, 4-methylphenyl, 3,4-dimethylphenyl, 2,4-dimethylphenyl, 2,5-dimethylphenyl, 2-ethylphenyl, 3-propylphenyl, 4-butylphenyl, 3,4-diethylphenyl, 2,4-diethylphenyl, 2,5-dipropylphenyl, 3,4,5-trimethylphenyl or 2-methylnaphthyl group; or a $C_{5-10}$-cycloalkyl- $C_{6-10}$-aryl group such as a 4-cyclohexylphenyl group.

Preferred examples of a substituted aralkyl group substituted by 1 to 3 groups selected from the members of Substituent Group B and Substituent Group C comprise a halo- $C_{7-12}$-aralkyl group such as a 2-fluorobenzyl, 3-bromophenethyl, 4-fluorobenzyl, 3,4-difluorobenzyl, 2,4-difluorobenzyl, 2,5-difluorobenzyl, 2-chlorophenethyl, 3-chlorobenzyl, 4-chlorobenzyl, 4-bromobenzyl, 4-chlorophenethyl, 3,4-dichlorobenzyl, 2,4-dichlorobenzyl, bis(2,4-dichlorophenyl)methyl, 2,5-dichlorobenzyl, 3,4,5-tribromobenzyl or 2-fluoronaphthylmethyl group; a $C_{1-4}$-alkoxyl- $C_{7-12}$-aralkyl group such as a 2-ethoxyphenethyl, 3-propoxybenzyl, 4-methoxybenzyl, 4-methoxyphenyldiphenylmethyl, 3,4-dimethoxyphenethyl, 2,4-dimethoxybenzyl, 2,5-dimethoxybenzyl, 3,4,5-trimethoxyphenethyl or 2-methoxynaphthylmethyl group; a $C_{2-5}$ alkoxycarbonyl-$C_{7-12}$-aralkyl group such as a 2-methoxycarbonylphenethyl, 4-ethoxycarbonylbenzyl or 2-methoxycarbonylnaphthylmethyl group; a nitro- $C_{7-12}$-aralkyl group such as a 2-nitrobenzyl, 3-nitrophenethyl, 4-nitrobenzyl, bis(2-nitrophenyl)methyl group; a cyano-$C_{7-12}$-aralkyl group such as a 2-cyanophenethyl, 3-cyanobenzyl, 4-cyanobenzyl, 4-cyanophenethyl or 4-cyanobenzyldiphenylmethyl group; a benzoyl-$C_{7-12}$-aralkyl group such as a 2-benzoylphenethyl, 3-benzoylbenzyl, 4-benzoylbenzyl or 2-benzoylnaphthylmethyl group; a halo-$C_{1-4}$-alkyl- $C_{7-12}$ aralkyl group such as a 2-trifluoromethylbenzyl, 3-trichloromethylphenethyl, 4-trifluoromethylbenzyl, 2,4-ditrifluoromethylbenzyl, 2,5-ditrifluoromethylphenethyl, 3,4,5-tris(trifluoromethyl)benzyl or 2-trifluoromethylnaphthylmethyl group; a $C_{1-4}$ alkyl-$C_{7-12}$-aralkyl group such as a 2-methylbenzyl, 3-methylbenzyl, 4-methylbenzyl, 4-methylphenethyl, 3,4-dimethylbenzyl, 2,4-dimethylphenethyl, 2,5-dimethylbenzyl, 2-ethylphenethyl, 3-propylphenethyl, 4-butylbenzyl, 3,4-diethylbenzyl, 2,4-diethylphenethyl, 2,5-dipropylbenzyl, 3,4,5-trimethylbenzyl, 2,4,6-trimethylbenzyl or 2-methylnaphthylmethyl group; or a $C_{5-10}$ cycloalkyl- $C_{7-12}$ aralkyl group such as a 4-cyclohexylbenzyl group.

Preferred examples of a substituted heterocyclyl group substituted by 1 to 3 groups selected from the members of Substituent Group B and Substituent Group C comprise a haloheterocyclyl group such as a 3-fluorotetrahydrobenzothiophen-2-yl, 3-bromopiperidin-4-yl, 2-fluoroquinolin-3-yl, 3-fluoromorpholin-2-yl, 3-fluoropiperazin-2-yl, 2-chloropiperidin-4-yl, 3-chlorotetrahydrobenzothiophen-2-yl, 4-chloropiperidin-2-yl or 2,6-dichloropiperidin-4-yl group; a $C_{1-4}$ alkoxy-heterocyclyl group such as a 3-ethoxymorpholin-2-yl, 4-methoxyquinolin-8-yl, 2,6-dimethoxypiperidin-4-yl group; a $C_{2-5}$ alkoxycarbonyl-heterocyclyl group such as a 3-methoxycarbonyltetrahydrobenzothiophen-2-yl or 4-ethoxycarbonyltetrahydrobenzothiophen-2-yl group; a cyanoheterocyclyl group such as a 3-cyanopyridin-2-yl, 3-cyanotetrahydrobenzothiophen-2-yl or 3-cyanopiperazin-2-yl group; a benzoylheterocyclyl group such as a 2-benzoylpiperidin-4-yl or 4-benzoylpyridin-2-yl group; a halo- $C_{1-4}$-alkyl- heterocyclyl group such as a 2-trifluoromethylquinolin-3-yl, 3-trichloromethylmethylmorpholin-2-yl, 4-trifluoromethyltetrahydrobenzothiophen-2-yl or 2,6-ditrifluoromethylpiperidin-4-yl group; a $C_{1-4}$-alkyl-heterocyclyl group such as a 3-methyltetrahydrobenzothiophen-2-yl, 4-methyltetrahydrobenzothiophen-2-yl, 4-methylpiperidin-2-yl or 2,6-dimethylpyridin-4-yl, 2,5-dimethylpyridin-4-yl group; or a $C_{5-10}$-cycloalkyl- heterocyclyl group such as a 4-cyclohexylpiperidin-2-yl group.

The compounds (I) of the present invention may exist in the form of salts. Preferred salts include a salt with an inorganic acid such as a hydrohalide salt, for example a hydrofluoride, hydrochloride, hydrobromide or hydroiodide salt, or a salt with another inorganic acid, for example a nitrate, perchlorate, sulfate or phosphate salt; a salt with an organic acid such as an alkanesulfonate salt, more especially an optionally halo substituted alkanesulfonate have having 1 to 3 carbon atoms in the alkane group and 0 to 5 halogen atom substituents, for example a methanesulfonate, trifluoromethanesulfonate, ethanesulfonate, trifluoromethanesulfonate or pentafluoroethanesulfonate salt, such as an arylsulfonate salt, more especially an optionally alkyl-substituted arylsulfonate having 0 to 3 alkyl substituents each having 1 to 3 carbon atoms, for example a benzenesulfonate or p-toluenesulfonate salt, or such as a salt with another organic acid, for example a fumarate, succinate, citrate, tartarate, oxalate or maleate salt; or such as a salt with an amino acid, for example a glutamate or aspartate salt. Preferred salts also include 'onium salts, such as those formed when a member of Substituent Group A is present as a substituent at a tertiary nitrogen, for example when a member of Subsituent Group A is a fourth group on a nitrogen atom itself being saturated and being the point of binding of a heterocyclic group $R^3$. Salts which are pharmaceutically acceptable salts form an aspect of the present invention.

The compounds of the present invention may exist in an optically active form. When an asymmetric carbon atom is present in the molecule, stereoisomers with R configuration or S configuration are possible. If m is 1 or 2, geometric isomers are possible. The present invention embraces all of these individual isomers and any mixture thereof.

Preferred compounds of formula (I) of the present invention include:

(1) Compounds in which $R^1$ is a nitro, amino or a protected amino group;
(2) Compounds in which $R^1$ is an amino or protected amino group;
(3) Compounds in which $R^1$ is an amino group;
(4) Compounds in which $R^2$ is an amino, protected amino or a hydroxy group;
(5) Compounds in which $R^2$ is an amino or protected amino group;
(6) Compounds in which $R^3$ is a substituted amino group substituted by 1 or 2 groups selected from the members of Substituent Group A as defined, or a heterocyclic group having the ring nitrogen atom as the point of binding;
(7) Compounds in which $R^3$ is a substituted amino group substituted by 1 or 2 groups selected from the members of Substituent Group A', or a heterocyclic group having the ring nitrogen atom as the point of binding;
(8) Compounds in which $R^3$ is a substituted amino group substituted by 1 or 2 groups selected from the members of Substituent Group A", or a heterocyclic group having the ring nitrogen atom as the point of binding;
(9) Compounds in which m is 0 or 1; and
(10) Compounds in which n is an integer from 2 to 6;

where Substituent Group A' consists of the following members: straight or branched chain alkyl groups having from 1 to 4 carbon atoms, 5- to 10-membered optionally bridged saturated cyclic hydrocarbon group, 6- to 10-membered aromatic cyclic hydrocarbon groups optionally fused with a cycloalkyl group and optionally substituted by 1 or 2 groups selected from the members of Substituent Group B and Substituent Group C, heterocyclyl groups, and heterocyclyl groups substituted by 1 or 2 groups selected from the members of Substituent Group B and Substituent Group C; and Substituent Group A" consists of the following members: straight or branched chain alkyl groups having from 1 to 4 carbon atoms, an adamantyl group, a phenyl group, and substituted phenyl groups substituted by 1 or 2 halogen atoms and/or straight or branched chain alkyl groups having from 1 to 4 carbon atoms.

Typical non-limiting compounds of formula (I) of the present invention are exemplified in the following Table, where these abbreviations are employed:

| | |
|---|---|
| Ac | acetyl |
| Ada | adamantyl |
| MCTB | 3-methoxycarbonyltetrahydrobenzothienyl |
| TFAc | trifluoroacetyl |
| Et | ethyl |
| Mor | morpholinyl |
| Pipe | piperidino |
| iBu | isobutyl |
| Pr | propyl |
| Bu | butyl |
| Me | methyl |
| Ph | phenyl |
| Quin | quinolyl |
| Ind | indanyl |

| Compound No. | $R^1$ | $R^2$ | $R^3$ | m | n |
|---|---|---|---|---|---|
| 1 | 4-AcO— | 3-NO$_2$— | 1-Ada—NH— | 1 | 0 |
| 2 | 4-HO— | 3-NO$_2$— | 1-Ada—NH— | 1 | 0 |
| 3 | 4-HO— | 3-NH$_2$— | 1-Ada—NH— | 0 | 2 |
| 4 | 4-HO— | 3-NH$_2$— | 2-MCTB—NH— | 0 | 3 |
| 5 | 4-HO— | 3-NH$_2$— | 1-Ada—NH— | 0 | 4 |
| 6 | 4-HO— | 3-NH$_2$— | 1-Ada—NH— | 0 | 5 |
| 7 | 4-HO— | 3-NH$_2$— | 1-Ada—NH— | 0 | 6 |
| 8 | 4-HO— | 3-NO$_2$— | 1-Ada—NH— | 1 | 0 |
| 9 | 4-HO— | 3-NH$_2$— | 1-Ada—NH— | 1 | 1 |
| 10 | 4-HO— | 3-NH$_2$— | 1-Ada—NH— | 1 | 2 |
| 11 | 4-HO— | 3-NH$_2$— | 1-Ada—NH— | 1 | 3 |
| 12 | 4-HO— | 3-NH$_2$— | 2-MCTB—NH— | 1 | 4 |
| 13 | 4-HO— | 3-NO$_2$— | 1-Ada—NH— | 1 | 5 |

-continued

| | | | | | |
|---|---|---|---|---|---|
| 14 | 4-HO— | 3-NH₂— | 1-Ada—NH— | 1 | 6 |
| 15 | 4-HO— | 3-NH₂— | 1-Ada—NH— | 2 | 0 |
| 16 | 4-HO— | 3-NH₂— | 1-Ada—NH— | 2 | 1 |
| 17 | 4-HO— | 3-NH₂— | 1-Ada—NH— | 2 | 2 |
| 18 | 4-HO— | 3-NO₂— | 1-Ada—NH— | 2 | 3 |
| 19 | 4-HO— | 3-NH₂— | 1-Ada—NH— | 2 | 4 |
| 20 | 4-HO— | 3-NH₂— | 1-Ada—NH— | 2 | 5 |
| 21 | 4-HO— | 3-NH₂— | 1-Ada—NH— | 2 | 6 |
| 22 | 3-AcO— | 4-NO₂— | 1-Ada—NH— | 1 | 0 |
| 23 | 3-HO— | 4-NO₂— | 1-Ada—NH— | 1 | 0 |
| 24 | 3-HO— | 4-NH₂— | 1-Ada—NH— | 0 | 2 |
| 25 | 3-HO— | 4-NH₂— | 1-Ada—NH— | 0 | 3 |
| 26 | 3-HO— | 4-NH₂— | 1-Ada—NH— | 0 | 4 |
| 27 | 3-HO— | 4-NO₂— | 1-Ada—NH— | 0 | 5 |
| 28 | 3-HO— | 4-NH₂— | 1-Ada—NH— | 0 | 6 |
| 29 | 3-HO— | 4-NH₂— | 1-Ada—NH— | 1 | 0 |
| 30 | 3-HO— | 4-NH₂— | 1-Ada—NH— | 1 | 1 |
| 31 | 3-HO— | 4-NH₂— | 1-Ada—NH— | 1 | 2 |
| 32 | 3-HO— | 4-NH₂— | 1-Ada—NH— | 1 | 3 |
| 33 | 3-HO— | 4-NO₂— | 2-MCTB—NH— | 1 | 4 |
| 34 | 3-HO— | 4-NH₂— | 1-Ada—NH— | 1 | 5 |
| 35 | 3-HO— | 4-NH₂— | 1-Ada—NH— | 1 | 6 |
| 36 | 3-HO— | 4-NH₂— | 1-Ada—NH— | 2 | 0 |
| 37 | 3-HO— | 4-NH₂— | 1-Ada—NH— | 2 | 1 |
| 38 | 3-HO— | 4-NO₂— | 1-Ada—NH— | 2 | 2 |
| 39 | 3-HO— | 4-NH₂— | 1-Ada—NH— | 2 | 3 |
| 40 | 3-HO— | 4-NH₂— | 1-Ada—NH— | 2 | 4 |
| 41 | 3-HO— | 4-NH₂— | 1-Ada—NH— | 2 | 5 |
| 42 | 3-HO— | 4-NH₂— | 1-Ada—NH— | 2 | 6 |
| 43 | 4-TFAcO— | 3-NO₂— | 1-Ada—NH— | 1 | 0 |
| 44 | 3-TFAcO— | 4-NO₂— | 1-Ada—NH— | 1 | 0 |
| 45 | 4-AcO— | 3-NO₂— | (Et)₂N— | 1 | 0 |
| 46 | 4-HO— | 3-NO₂— | (Et)₂N— | 1 | 0 |
| 47 | 4-HO— | 3-NH₂— | (Et)₂N— | 0 | 2 |
| 48 | 4-HO— | 3-NH₂— | (Et)₂N— | 0 | 3 |
| 49 | 4-HO— | 3-NH₂— | (Et)₂N— | 0 | 4 |
| 50 | 4-HO— | 3-NO₂— | (Et)₂N— | 1 | 0 |
| 51 | 4-HO— | 3-NH₂— | 2,4-diMePh—NH— | 1 | 1 |
| 52 | 4-HO— | 3-NH₂— | (Et)₂N— | 1 | 2 |
| 53 | 4-HO— | 3-NH₂— | (Et)₂N— | 1 | 3 |
| 54 | 4-HO— | 3-NO₂— | (Me)₂N— | 1 | 5 |
| 55 | 4-HO— | 3-NH₂— | (Et)₂N— | 2 | 0 |
| 56 | 4-HO— | 3-NH₂— | (Et)₂N— | 2 | 1 |
| 57 | 4-HO— | 3-NH₂— | (Et)₂N— | 2 | 2 |
| 58 | 4-HO— | 3-NO₂— | (Me)₂N— | 2 | 3 |
| 59 | 4-HO— | 3-NH₂— | 2,4-diMePh—NH— | 2 | 4 |
| 60 | 4-HO— | 3-NH₂— | (Et)₂N— | 2 | 6 |
| 61 | 3-AcO— | 4-NO₂— | (Et)₂N— | 1 | 0 |
| 62 | 3-HO— | 4-NO₂— | (Et)₂N— | 1 | 0 |
| 63 | 3-HO— | 4-NH₂— | (Et)₂N— | 0 | 2 |
| 64 | 3-HO— | 4-NH₂— | 2,4-diMePh—NH— | 0 | 3 |
| 65 | 3-HO— | 4-NO₂— | (Et)₂N— | 0 | 4 |
| 66 | 3-HO— | 4-NH₂— | (Et)₂N— | 1 | 0 |
| 67 | 3-HO— | 4-NH₂— | 2,4-diMePh—NH— | 1 | 1 |
| 68 | 3-HO— | 4-NH₂— | (Et)₂N— | 1 | 2 |
| 69 | 3-HO— | 4-NH₂— | (Et)₂N— | 1 | 3 |
| 70 | 3-HO— | 4-NO₂— | (Et)₂N— | 1 | 4 |
| 71 | 3-HO— | 4-NH₂— | (Et)₂N— | 2 | 0 |
| 72 | 3-HO— | 4-NH₂— | (Et)₂N— | 2 | 1 |
| 73 | 3-HO— | 4-NO₂— | (Et)₂N— | 2 | 2 |
| 74 | 4-TFAcO— | 3-NO₂— | (Et)₂N— | 1 | 0 |
| 75 | 3-TFAcO— | 4-NO₂— | (Et)₂N— | 1 | 0 |
| 76 | 4-AcO— | 3-NO₂— | 1-Mor— | 1 | 0 |
| 77 | 4-HO— | 3-NO₂— | 1-Mor— | 1 | 0 |
| 78 | 4-HO— | 3-NH₂— | 1-Mor— | 0 | 2 |
| 79 | 4-HO— | 3-NH₂— | 1-Mor— | 0 | 3 |
| 80 | 4-HO— | 3-NH₂— | Pipe— | 0 | 4 |
| 81 | 4-HO— | 3-NO₂— | 1-Mor— | 1 | 0 |
| 82 | 4-HO— | 3-NH₂— | 1-Mor— | 1 | 1 |
| 83 | 4-HO— | 3-NH₂— | 1-Mor— | 1 | 2 |
| 84 | 4-HO— | 3-NH₂— | 1-Mor— | 1 | 3 |
| 85 | 4-HO— | 3-NH₂— | 1-Mor— | 1 | 4 |
| 86 | 3-AcO— | 4-NO₂— | 1-Mor— | 1 | 0 |
| 87 | 3-HO— | 4-NO₂— | 1-Mor— | 1 | 0 |
| 88 | 3-HO— | 4-NH₂— | Pipe— | 0 | 2 |
| 89 | 3-HO— | 4-NH₂— | 1-Mor— | 0 | 3 |
| 90 | 3-HO— | 4-NH₂— | 1-Mor— | 0 | 4 |
| 91 | 3-HO— | 4-NH₂— | 1-Mor— | 1 | 0 |
| 92 | 3-HO— | 4-NH₂— | 1-Mor— | 1 | 1 |
| 93 | 3-HO— | 4-NH₂— | Pipe— | 1 | 2 |

-continued

| | | | | | |
|---|---|---|---|---|---|
| 94 | 3-HO— | 4-NH$_2$— | 1-Mor— | 1 | 3 |
| 95 | 3-HO— | 4-NO$_2$— | 1-Mor— | 1 | 4 |
| 96 | 3-HO— | 4-NH$_2$— | 1-Mor— | 2 | 0 |
| 97 | 3-HO— | 4-NH$_2$— | 1-Mor— | 2 | 1 |
| 98 | 3-HO— | 4-NO$_2$— | 1-Mor— | 2 | 2 |
| 99 | 3-HO— | 4-NH$_2$— | Pipe— | 2 | 3 |
| 100 | 3-HO— | 4-NH$_2$— | 1-Mor— | 2 | 4 |
| 101 | 4-TFAcO— | 3-NO$_2$— | 1-Mor— | 1 | 0 |
| 102 | 3-TFAcO— | 4-NO$_2$— | 1-Mor— | 1 | 0 |
| 103 | 4-AcO— | 3-NO$_2$— | iBu—NH— | 1 | 0 |
| 104 | 4-HO— | 3-NO$_2$— | iBu—NH— | 1 | 0 |
| 105 | 4-HO— | 3-NH$_2$— | iBu—NH— | 0 | 2 |
| 106 | 4-HO— | 3-NH$_2$— | iBu—NH— | 0 | 3 |
| 107 | 4-HO— | 3-NH$_2$— | Pr—NH— | 0 | 4 |
| 108 | 4-HO— | 3-NH$_2$— | Me—NH— | 0 | 5 |
| 109 | 4-HO— | 3-NH$_2$— | Et—NH— | 0 | 6 |
| 110 | 4-HO— | 3-NO$_2$— | iBu—NH— | 1 | 0 |
| 111 | 4-HO— | 3-NH$_2$— | iBu—NH— | 1 | 1 |
| 112 | 4-HO— | 3-NH$_2$— | Me—NH— | 1 | 2 |
| 113 | 4-HO— | 3-NH$_2$— | Et—NH— | 1 | 3 |
| 114 | 4-HO— | 3-NH$_2$— | Bu—NH— | 1 | 4 |
| 115 | 4-HO— | 3-NO$_2$— | Bu—NH— | 1 | 5 |
| 116 | 4-HO— | 3-NH$_2$— | Bu—NH— | 1 | 6 |
| 117 | 4-HO— | 3-NH$_2$— | iBu—NH— | 2 | 0 |
| 118 | 4-HO— | 3-NH$_2$— | iBu—NH— | 2 | 1 |
| 119 | 4-HO— | 3-NH$_2$— | iBu—NH— | 2 | 2 |
| 120 | 4-HO— | 3-NO$_2$— | iBu—NH— | 2 | 3 |
| 121 | 4-HO— | 3-NH$_2$— | iBu—NH— | 2 | 4 |
| 122 | 4-HO— | 3-NH$_2$— | Bu—NH— | 2 | 5 |
| 123 | 4-HO— | 3-NH$_2$— | Pr—NH— | 2 | 6 |
| 124 | 3-AcO— | 4-NO$_2$— | iBu—NH— | 1 | 0 |
| 125 | 3-HO— | 4-NO$_2$— | iBu—NH— | 1 | 0 |
| 126 | 3-HO— | 4-NH$_2$— | iBu—NH— | 0 | 2 |
| 127 | 3-HO— | 4-NH$_2$— | iBu—NH— | 0 | 3 |
| 128 | 3-HO— | 4-NH$_2$— | iBu—NH— | 0 | 4 |
| 129 | 3-HO— | 4-NH$_2$— | iBu—NH— | 1 | 0 |
| 130 | 3-HO— | 4-NH$_2$— | iBu—NH— | 1 | 1 |
| 131 | 3-HO— | 4-NH$_2$— | iBu—NH— | 1 | 2 |
| 132 | 3-HO— | 4-NH$_2$— | iBu—NH— | 1 | 3 |
| 133 | 3-HO— | 4-NO$_2$— | iBu—NH— | 1 | 4 |
| 134 | 3-HO— | 4-NH$_2$— | iBu—NH— | 2 | 0 |
| 135 | 3-HO— | 4-NH$_2$— | iBu—NH— | 2 | 1 |
| 136 | 3-HO— | 4-NO$_2$— | iBu—NH— | 2 | 2 |
| 137 | 3-HO— | 4-NH$_2$— | iBu—NH— | 2 | 3 |
| 138 | 3-HO— | 4-NH$_2$— | iBu—NH— | 2 | 4 |
| 139 | 3-HO— | 4-NH$_2$— | iBu—NH— | 2 | 5 |
| 140 | 4-TFAcO— | 3-NO$_2$— | iBu—NH— | 1 | 0 |
| 141 | 3-TFAcO— | 4-NO$_2$— | iBu—NH— | 1 | 0 |
| 142 | 4-AcO— | 3-NO$_2$— | (Ph)$_2$N— | 1 | 0 |
| 143 | 4-HO— | 3-NO$_2$— | (Ph)$_2$N— | 1 | 0 |
| 144 | 4-HO— | 3-NH$_2$— | (Ph)$_2$N— | 0 | 2 |
| 145 | 4-HO— | 3-NH$_2$— | PhNH— | 0 | 3 |
| 146 | 4-HO— | 3-NH$_2$— | PhNH— | 0 | 4 |
| 147 | 4-HO— | 3-NH$_2$— | PhNH— | 0 | 5 |
| 148 | 4-HO— | 3-NH$_2$— | (Ph)$_2$N— | 0 | 6 |
| 149 | 4-HO— | 3-NO$_2$— | (Ph)$_2$N— | 1 | 0 |
| 150 | 4-HO— | 3-NH$_2$— | (Ph)$_2$N— | 1 | 1 |
| 151 | 4-HO— | 3-NH$_2$— | (Ph)$_2$N— | 1 | 2 |
| 152 | 4-HO— | 3-NH$_2$— | (Ph)$_2$N— | 1 | 3 |
| 153 | 4-HO— | 3-NH$_2$— | (Ph)$_2$N— | 1 | 4 |
| 154 | 4-HO— | 3-NH$_2$— | (Ph)$_2$N— | 2 | 0 |
| 155 | 4-HO— | 3-NH$_2$— | (Ph)$_2$N— | 2 | 1 |
| 156 | 4-HO— | 3-NH$_2$— | (Ph)$_2$N— | 2 | 2 |
| 157 | 4-HO— | 3-NO$_2$— | (Ph)$_2$N— | 2 | 3 |
| 158 | 4-HO— | 3-NH$_2$— | (Ph)$_2$N— | 2 | 4 |
| 159 | 3-AcO— | 4-NO$_2$— | (Ph)$_2$N— | 1 | 0 |
| 160 | 3-HO— | 4-NO$_2$— | (Ph)$_2$N— | 1 | 0 |
| 161 | 3-HO— | 4-NH$_2$— | (Ph)$_2$N— | 0 | 2 |
| 162 | 3-HO— | 4-NH$_2$— | (Ph)$_2$N— | 0 | 3 |
| 163 | 3-HO— | 4-NH$_2$— | (Ph)$_2$N— | 0 | 4 |
| 164 | 3-HO— | 4-NH$_2$— | (Ph)$_2$N— | 1 | 0 |
| 165 | 3-HO— | 4-NH$_2$— | (Ph)$_2$N— | 1 | 1 |
| 166 | 3-HO— | 4-NH$_2$— | (Ph)$_2$N— | 1 | 2 |
| 167 | 3-HO— | 4-NH$_2$— | 2,4-diClPh—NH— | 1 | 3 |
| 168 | 3-HO— | 4-NO$_2$— | 2,4-diClPh—NH— | 1 | 4 |
| 169 | 3-HO— | 4-NH$_2$— | (Ph)$_2$N— | 1 | 5 |
| 170 | 3-HO— | 4-NH$_2$— | 2,4-diClPh—NH— | 1 | 6 |
| 171 | 3-HO— | 4-NH$_2$— | (Ph)$_2$N— | 2 | 0 |
| 172 | 3-HO— | 4-NH$_2$— | 2,4-diClPh—NH— | 2 | 1 |
| 173 | 3-HO— | 4-NO$_2$— | 2,4-diClPh—NH— | 2 | 2 |

-continued

| | | | | | |
|---|---|---|---|---|---|
| 174 | 3-HO— | 4-NH₂— | (Ph)₂N— | 2 | 3 |
| 175 | 3-HO— | 4-NH₂— | 2,4-diClPh—NH— | 2 | 4 |
| 176 | 3-HO— | 4-NH₂— | (Ph)₂N— | 2 | 5 |
| 177 | 3-HO— | 4-NH₂— | (Ph)₂N— | 2 | 6 |
| 178 | 4-TFAcO— | 3-NO₂— | (Ph)₂N— | 1 | 0 |
| 179 | 3-TFAcO— | 4-NO₂— | (Ph)₂N— | 1 | 0 |
| 180 | 4-TFAc—NH— | 3-NO₂— | 1-Ada—NH— | 1 | 0 |
| 181 | 3-TFAc—NH— | 4-NO₂— | 1-Ada—NH— | 1 | 0 |
| 182 | 4-NH₂— | 3-NO₂— | 1-Ada—NH— | 1 | 0 |
| 183 | 3-NH₂— | 4-NO₂— | 1-Ada—NH— | 1 | 0 |
| 184 | 4-NH₂— | 3-NH₂— | 1-Ada—NH— | 1 | 0 |
| 185 | 4-TFAc—NH— | 3-NO₂— | 1-Ada—NH— | 1 | 1 |
| 186 | 3-TFAc—NH— | 4-NO₂— | 1-Ada—NH— | 1 | 1 |
| 187 | 4-NH₂— | 3-NO₂— | 1-Ada—NH— | 1 | 1 |
| 188 | 3-NH₂— | 4-NO₂— | 1-Ada—NH— | 1 | 1 |
| 189 | 4-NH₂— | 3-NH₂— | 1-Ada—NH— | 1 | 1 |
| 190 | 4-TFAc—NH— | 3-NO₂— | 1-Ada—NH— | 0 | 2 |
| 191 | 3-TFAc—NH— | 4-NO₂— | 1-Ada—NH— | 0 | 2 |
| 192 | 4-NH₂— | 3-NO₂— | 1-Ada—NH— | 0 | 2 |
| 193 | 3-NH₂— | 4-NO₂— | 1-Ada—NH— | 0 | 2 |
| 194 | 4-NH₂— | 3-NH₂— | 1-Ada—NH— | 0 | 2 |
| 195 | 4-TFAc—NH— | 3-NO₂— | (Et)₂N— | 1 | 0 |
| 196 | 3-TFAc—NH— | 4-NO₂— | 1-Mor— | 1 | 0 |
| 197 | 4-NH₂— | 3-NO₂— | (Ph)₂N— | 1 | 0 |
| 198 | 3-NH₂— | 4-NO₂— | (Et)₂N— | 1 | 0 |
| 199 | 4-NH₂— | 3-NH₂— | Bu—NH— | 1 | 0 |
| 200 | 4-TFAc—NH— | 3-NO₂— | iBu—NH— | 1 | 1 |
| 201 | 3-TFAc—NH— | 4-NO₂— | (Ph)₂N— | 1 | 1 |
| 202 | 4-NH₂— | 3-NO₂— | (Et)₂N— | 1 | 1 |
| 203 | 3-NH₂— | 4-NO₂— | (Ph)₂N— | 1 | 1 |
| 204 | 4-NH₂— | 3-NH₂— | 1-Mor— | 1 | 1 |
| 205 | 4-TFAc—NH— | 3-NO₂— | (Ph)₂N— | 0 | 2 |
| 206 | 3-TFAc—NH— | 4-NO₂— | (Et)₂N— | 0 | 2 |
| 207 | 4-NH₂— | 3-NO₂— | Pipe— | 0 | 2 |
| 208 | 3-NH₂— | 4-NO₂— | iBu—NH— | 0 | 2 |
| 209 | 4-NH₂— | 3-NH₂— | (Et)₂N— | 0 | 2 |
| 210 | 4-TFAc—NH— | 3-NO₂— | 1-Ada—NH— | 0 | 3 |
| 211 | 4-NH₂— | 3-NO₂— | 1-Ada—NH— | 0 | 3 |
| 212 | 4-NH₂— | 3-NH₂— | 1-Ada—NH— | 0 | 3 |
| 213 | 4-TFAc—NH— | 3-NO₂— | 2,4-diClPh—NH— | 1 | 0 |
| 214 | 3-TFAc—NH— | 4-NO₂— | 2,4-diClPh—NH— | 1 | 0 |
| 215 | 4-NH₂— | 3-NO₂— | 2,4-diClPh—NH— | 1 | 0 |
| 216 | 3-NH₂— | 4-NO₂— | 2,4-diClPh—NH— | 1 | 0 |
| 217 | 4-NH₂— | 3-NH₂— | 2,4-diClPh—NH— | 1 | 0 |
| 218 | 4-TFAc—NH— | 3-NO₂— | 2,4-diClPh—NH— | 1 | 1 |
| 219 | 3-TFAc—NH— | 4-NO₂— | 2,4-diClPh—NH— | 1 | 1 |
| 220 | 4-NH₂— | 3-NO₂— | 2,4-diClPh—NH— | 1 | 1 |
| 221 | 3-NH₂— | 4-NO₂— | 2,4-diClPh—NH— | 1 | 1 |
| 222 | 4-NH₂— | 3-NH₂— | 2,4-diClPh—NH— | 1 | 1 |
| 223 | 4-TFAc—NH— | 3-NO₂— | 2,4-diClPh—NH— | 0 | 2 |
| 224 | 3-TFAc—NH— | 4-NO₂— | 2,4-diClPh—NH— | 0 | 2 |
| 225 | 4-NH₂— | 3-NO₂— | 2,4-diClPh—NH— | 0 | 2 |
| 226 | 3-NH₂— | 4-NO₂— | 2,4-diClPh—NH— | 0 | 2 |
| 227 | 4-NH₂— | 3-NH₂— | 2,4-diClPh—NH— | 0 | 2 |
| 228 | 4-TFAc—NH— | 3-NO₂— | 2,4-diClPh—NH— | 0 | 3 |
| 229 | 4-NH₂— | 3-NO₂— | 2,4-diClPh—NH— | 0 | 3 |
| 230 | 4-NH₂— | 3-NH₂— | 2,4-diClPh—NH— | 0 | 3 |
| 231 | 4-TFAc—NH— | 3-NO₂— | 2,5-diMePh—NH— | 0 | 2 |
| 232 | 4-NH₂— | 3-NO₂— | 2,5-diMePh—NH— | 0 | 2 |
| 233 | 4-NH₂— | 3-NH₂— | 2,5-diMePh—NH— | 0 | 2 |
| 234 | 4-TFAc—NH— | 3-NO₂— | (Ph)₂N— | 0 | 2 |
| 235 | 4-NH₂— | 3-NO₂— | (Ph)₂N— | 0 | 2 |
| 236 | 4-NH₂— | 3-NH₂— | (Ph)₂N— | 0 | 2 |
| 237 | 4-TFAc—NH— | 3-NO₂— | 4-PhCO—Ph—NH— | 0 | 2 |
| 238 | 4-NH₂— | 3-NO₂— | 4-PhCO—Ph—NH— | 0 | 2 |
| 239 | 4-NH₂— | 3-NH₂— | 4-PhCO—Ph—NH— | 0 | 2 |
| 240 | 4-TFAc—NH— | 3-NO₂— | Pipe— | 0 | 2 |
| 241 | 4-NH₂— | 3-NH₂— | Pipe— | 0 | 2 |
| 242 | 4-TFAc—NH— | 3-NO₂— | (Ph)(Me)N— | 0 | 2 |
| 243 | 4-NH₂— | 3-NO₂— | (Ph)(Me)N— | 0 | 2 |
| 244 | 4-NH₂— | 3-NH₂— | (Ph)(Me)N— | 0 | 2 |
| 245 | 4-AcO— | 3-NO₂— | 1-Ind—NH— | 1 | 0 |
| 246 | 4-HO— | 3-NO₂— | 1-Ind—NH— | 1 | 0 |
| 247 | 4-HO— | 3-NH₂— | 1-Ind—NH— | 0 | 2 |
| 248 | 4-TFAc—NH— | 3-NO₂— | 3-Quin—NH— | 0 | 2 |
| 249 | 4-NH₂— | 3-NH₂— | 3-Quin—NH— | 0 | 2 |
| 250 | 4-NH₂— | 3-NH₂— | 3-Quin—NH— | 0 | 2 |
| 251 | 4-NH₂— | 3-NH₂— | 3-Quin—NH—.HCl | 0 | 2 |
| 252 | 4-NO₂— | 3-TFAc—NH— | 3-Quin—NH— | 0 | 2 |
| 253 | 4-NO₂— | 3-NH₂— | 3-Quin—NH— | 0 | 2 |

-continued

| 254 | 4-TFAc—NH— | 3-NO$_2$— | 5-Quin—NH— | 0 | 2 |
| 255 | 4-NH$_2$— | 3-NO$_2$— | 5-Quin—NH— | 0 | 2 |
| 256 | 4-NH$_2$— | 3-NH$_2$— | 5-Quin—NH— | 0 | 2 |
| 257 | 4-NH$_2$— | 3-NH$_2$— | 5-Quin—NH—.HCl | 0 | 2 |
| 258 | 4-TFAc—NH— | 3-NO$_2$— | 8-Quin—NH— | 0 | 2 |
| 259 | 4-NH$_2$— | 3-NO$_2$— | 8-Quin—NH— | 0 | 2 |
| 260 | 4-NH$_2$— | 3-NH$_2$— | 8-Quin—NH— | 0 | 2 |
| 261 | 4-NH$_2$— | 3-NH$_2$— | 8-Quin—NH—.HCl | 0 | 2 |

Preferred compounds among those mentioned above are those numbered: 1, 2, 4, 5, 6, 7, 8, 9, 15, 24, 25, 26, 29, 47, 48, 49, 64, 66, 78, 79, 80, 82, 87, 88, 89, 90, 91, 105, 106, 107, 126, 127, 128, 129, 144, 145, 146, 147, 161, 162, 163, 167, 169, 170, 172, 174, 175, 184, 185, 189, 190, 192, 194, 199, 204, 209, 210, 212, 217, 222, 227, 228, 230, 236, 239, 247, 250, 256 and 260, and salts thereof.

The more preferred compounds are those numbered: 4, 5, 25, 29, 64, 79, 91, 145, 146, 184, 189, 194, 210, 212, 227, 230, 236, 239, 247, 250, 256, 260, and salts therof.

The most preferred compounds are those numbered: 4, 5, 25, 29, 79, 91, 184, 189, 194, 212, 227, 230, 236, 239, 247, 250, 256 and 260, and salts thereof, especially compounds 250, 251, 256, 257, 260 and 261.

NGF Promoter Activity

Furukawa et al. have reported that fibroblast-forming L-M cells from mouse connective tissue can produce and secrete a relatively large amount of NGF, and that catecholamines accelerate such production and secretion of NGF (J. Biol. Chem., 261, 6039–6047, 1986). Following the test method described in this Furukawa paper, but using the compounds of the invention and recognized NGF promoters epinephrine, isoproterenol, L-DOPA, and caffeic acid, NGF production and secretion activities were examined. The test compounds of this invention were employed at 10 γ/ml, and the known compounds were employed at 20 γ/ml.

Culture medium 199 containing 0.5% peptone was used for culturing L-M cells (for the culture medium 199, see, for instance, Morgan et al., Proc. Soc. Exp. Biol. Med., 73, 1 (1950) or Morgan et al. J. Natl. Cancer Inst., 16, 557 (1955). About 5×10$^4$ of L-M cells were placed in each well of a culture plate with 24 wells, and cultured using a CO$_2$ incubator (37° C., 5% CO$_2$) until confluence. After removing the culture medium, the cultured cells were washed once with a wash solution which was 199 culture medium containing 0.5% bovine serum albumin (Fraction V, Sigma). The test compounds were added to a specified concentration to a 199 culture medium containing 0.5% bovine serum albumin, and used to treat 0.5 ml of L-M cells. After culturing the L-M cells in a CO$_2$ incubator for 24 hours, the medium was recovered and the NGF level was determined.

NGF was quantitatively determined using an enzyme immunoassay [Korshing, Thoenen, et al. Proc. Natl. Acad. Sci. USA, 80, 3513–3516, (1983)]. 75 μl of a solution of anti-mouse β-NGF antibody (0.3 μg/ml, pH 9.6; Boehringer Mannheim) was pipetted into each well of a polystyrene plate with 96 wells. After allowing the plate to stand at room temperature for an hour, the antibody was removed by washing three times with the wash solution. 50 μl of a solution of standard β-NGF (Wako Pure Chemical Industries Ltd.) or of the recovered medium was pipetted into the wells. After allowing the plate to stand for 68 hours at room temperature, the standard β-NGF or test solution was removed and each well was washed three times. 50 μl of a solution of β-NGF monoclonal antibody (100 mU/ml, pH 7.0; Boehringer Mannheim) labelled with β-galactosidase was pipetted into each well. After allowing the plate to stand at 4° C. for 15–18 hours, enzyme labelled antibody was removed and the wells washed three times followed by pipetting 100 μl of a solution of chlorophenol red-β-D-galactopyranoside (1 mg/ml, pH 7.3; Boehringer Mannheim) into each well. Color was allowed to develop (after 2–3 hours at room temperature), and the absorbance was determined at 570 nm.

The amount of NGF was calculated from a standard curve. The results are expressed as a relative value (%) which is relative to the amount of NGF produced and secreted by cells treated not with the test compounds. The numerical values (% Control) are expressed by the mean value in the 3 wells of the control (without addition of the test compounds).

| Known compound | % Control |
| --- | --- |
| epinephrine | 140 ± 24 |
| isoproterenol | 168 ± 22 |
| L-DOPA | 117 ± 7 |
| caffeic Acid | 123 ± 14 |

| Example Compound | % Control |
| --- | --- |
| Example 22 | 380 |
| Example 34 | 606 |
| Example 40 | 276 |
| Example 43 | 491 |
| Example 53 | 315 |

It can be seen that the novel phenyl derivatives of the present invention include compounds which exhibit excellent activity in promoting the production and secretion of NGF. They are also low in toxicity. The active derivatives are thus of use in the therapy of dementia, cerebral ischemia and various kinds of nerve dysfunction.

The present invention therefore provides pharmaceutical compositions which comprise a compound of general formula (I), with the exception of intermediate compounds where R$^1$ is a nitro group, together with a pharmaceutically acceptable carrier.

Examples of administration routes for the active compounds (I) of the present invention include oral administration by formulation of the pharmaceutical composition as tablets, capsules, granules, or syrups; and parentheral administration by formulation as injections or suppositories. The pharmaceutical compositions can be prepared using appropriate additives such as vehicles, binders, disintegrators, lubricants, stabilizers or corrigents, according to the conventional procedures. The dosage may vary depending on the symptoms and age of a patient, but usually is from 0.1 to 1000 mg/kg a day, preferably from 1 to 100 mg/kg a day, which in general may be administered to human adults once per day or divided into several doses.

The compounds of the present invention of the general formula (I) can be prepared by a process provided by this invention, which comprises amide formation through reaction of a reactive carboxylic acid derivative of general formula (II) with a compound of general formula (III) to give a compound in accordance with this invention of formula (I'), in accordance with the following reaction scheme:

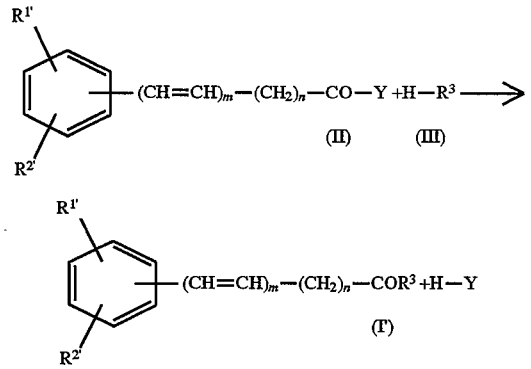

[wherein $R^{1'}$ represents a nitro group, a substituted amino group substituted by 1 or 2 groups selected from the members of Substituent Group A as defined in claim 1, or a protected amino group; $R^{2'}$ represents a substituted amino group substituted by 1 or 2 groups selected from the members of Substituent Group A as defined in claim 1, a protected amino group, a substituted hydroxy group substituted by a group selected from the members of Substitutent Group A as defined in claim 1, or a protected hydroxy group; Y represents a leaving group and $R^3$, m and n have the meanings given above], followed if necessary or desired by optional conversion of the product to another compound of this invention, for instance as follows:

(1) when $R^{1'}$ is a nitro group, reductive conversion into a compound of general formula (I) wherein $R^1$ is an amino group, (2) when $R^{1'}$ is a protected amino group, removal of the protecting group, and/or (3) when $R^{2'}$ is a protected amino or a protected hydroxy group, removal of the protecting group.

The process includes reacting a reactive carboxylic acid derivative of general formula (II) with a compound of the general formula (III). This reaction is suitably carried out in an inert solvent in the presence of a base, and proceeds with formation of compound (I') and HY.

The nature of the leaving group Y is not critical, and Y is suitably a leaving group of the kind conventionally employed for such a nucleophilic reaction of amide formation. Typically, the leaving group Y is a halogen atom such as chlorine, bromine or iodine; an alkanesulfonyloxy group having from 1 to 6 carbon atoms in the alkane group, such as a methanesulfonyloxy or ethanesulfonyloxy group; a haloalkanesulfonyloxy group having from 1 to 3 carbon atoms in the alkane group and 1 to 6 halo substuents, such as a trifluoromethanesulfonyloxy or pentafluoroethanesulfonyloxy group; or an arylsulfonyloxy group optionally having from 1 to 3 alkyl substituents each having from 1 to 3 carbon atoms, such as a benzenesulfonyloxy or p-toluenesulfonyloxy group. For preference, the group Y is a halogen atom.

The identity of the inert solvent is not particularly limited, provided that the solvent does not affect the reaction and can dissolve the starting materials to some extent. Examples of preferred solvents include aromatic hydrocarbons such as benzene, toluene or xylene; halohydrocarbons such as methylene chloride or chloroform; or ethers such as diethyl ether, diisopropyl ether, tetrahydrofuran or dioxane.

The identity of the base is also not particularly limited, provided that the base is effective in such a reaction. Examples of preferred bases include organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]nona-5-ene, 1,4-diazabicyclo[2.2.2] octane (DABCO) or 1,8-diazabicyclo[5.4.0]undec-7-ene (DBU).

The reaction of amide formation may be encouraged to proceed more effectively by the addition of a quarternary ammonium salt such as benzyltriethylammonium chloride or tetrabutylammonium chloride, or a crown ether such as dibenzyl-18-crown-6.

The reaction is preferably carried out at a temperature from –10° to 50° C., more preferably at from 0° to 30° C., and usually takes from 1 to 3 hours, though the time varies with factors such as the reaction temperature, the identity of the starting compounds, reaction reagents and inert solvent.

After completion of the amide formation reaction, the desired compound of general formula (I') of the present invention can be obtained from the reaction mixture by the use of conventional isolation methods. For example, the reaction mixture is suitably neutralized, and, after filtering off any insoluble matter off, a water-immiscible organic solvent is added. The solvent extract can then be separated, washed with water, and distilled to remove the solvent, thereby giving the target compound. If necessary, the target compound can be further purified by conventional techniques such as recrystallization, reprecipitation and/or chromatography.

One or more of the optional conversions can be effected. The order is not critical, and different deprotection reactions can be effected simultaneously. Isolation of the product of the amide reaction may not be necessary before the conversion can be carried out.

The optional conversion (1), where a nitro group is converted to an amino group, can be performed by customary methods available for reduction of nitro groups to amino groups. Suitable reduction methods include:

(a) reaction using a metal such as sodium amalgam, or a transition metal such as tin, zinc, iron, titanium trichloride or tin dichloride. A suitable solvent system comprises aqueous methanol, aqueous acetone, aqueous tetrahydrofuran, usually with hydrochloric acid and optionally with the inclusion of ammonium chloride. Examples of solvents include ammonium chloride/water-methanol or water-hydrochloric acid-acetone;

(b) reaction using a hydride such as an alkali metal borohydride, for example sodium borohydride or lithium borohydride; an aluminum hydride, for example lithium aluminum hydride or lithium triethoxyaluminohydride; or another hydride reagent, for example sodium tellurium hydride, in an ether such as ether or tetrahydrofuran, or in a mixed solvent thereof. Additionally in the case of using sodium borohydride or sodium tellurium hydride, the solvent can be an alcohol such as methanol or ethanol;

(c) catalytic reduction at room temperature using a catalyst such as palladium-carbon, platinum or Raney nickel in an alcohol such as methanol or ethanol, an ether such as tetrahydrofuran or dioxane, a fatty acid such as acetic acid, or a mixed solvent thereof with water;

(d) reaction using a Lewis acid such as aluminum chloride, tin tetrachloride or titanium tetrachloride together with a hydrogenated silyl compound such as hydrotriethylsilane or hydrotriphenylsilane; or (e) reduction by a radical reducing agent such as hydrotributyltin, hydrotriphenyltin or hydrodibutyltin together with a radical initiator such as azobisisobutyronitrile or triphenylboron as a catalyst.

Of these methods, a conventional catalytic reduction according to method (c) is preferred.

The optional conversion (2), where an amino protecting group is removed, and also that part of optional conversion (3) where an amino protecting group is removed, can be performed by customary methods which vary depending on the nature of the actual protecting group.

Where the amino protecting group is a silyl group, it can be removed by treatment with a compound capable of generating a fluoride anion, such as tetrabutylammonium fluoride. The treatment is typically effected in a solvent. The identity of the solvent is not particularly limited provided that it does not affect the reaction. An ether such as tetrahydrofuran or dioxane is preferably employed. The reaction temperature and reaction time are also not particularly limited, and usually the silyl deprotection reaction is carried out at room temperature requiring from 10 to 18 hours.

Where the amino protecting group is an aliphatic acyl group, an aromatic acyl group, an alkoxycarbonyl group or a substituted methylene group forming a Schiff base, deprotection can be effected by treatment with an acid or a base in the presence of an aqueous solvent. When an acid is used, the identity of the acid is not particularly limited, and preferably is an inorganic acid such as hydrochloric acid, sulfuric acid, phosphoric acid or hydrobromic acid. When a base is used, the identity of the base is not particularly limited, provided that it does not affect the rest of the compound, and preferably is an metal alkoxide such as sodium methoxide; an alkali metal carbonate such as sodium carbonate or potassium carbonate; an alkali metal hydroxide such as sodium hydroxide or potassium hydroxide; or ammonia such as in the form of aqueous ammonia solution or concentrated ammonia-methanol. The choice of solvent is not particularly limited, typically being one usually employed for hydrolytic reactions, and is preferably water; an organic solvent, for example an alcohol such as methanol, ethanol or propanol, or an ether such as tetrahydrofuran or dioxane; or a mixed solvent of water and an organic solvent. The suitable reaction temperature and reaction time will vary depending on the starting materials and acid or base employed and are thus not particularly restricted. In order to minimize side reactions, the deprotection is usually carried out at from 0° to 150° C. requiring from 1 to 10 hours.

Where the amino protecting group is an aralkyl group or an aralkyloxycarbonyl group, there is a variety of deprotectoin methods which can be employed. In general, it can be removed by contact with a reducing agent in a solvent, preferably by catalytic reduction using a catalyst at room temperature, by using an oxidizing agent, by treatment with an alkali metal, or by treatment with a halide.

The selection of a solvent for deprotection by catalytic reduction is not particularly limited provided that it does not participate in the reaction, and is preferably an alcohol such as methanol, ethanol or isopropanol; an ether such as diethyl ether, tetrahydrofuran or dioxane; an aromatic hydrocarbon such as toluene, benzene or xylene; an aliphatic hydrocarbon such as hexane or cyclohexane; an ester such as ethyl acetate or propyl acetate; a fatty acid such as acetic acid; or a mixed solvent thereof with water. The choice of catalyst is also not particularly restricted and can be one usually employed for catalytic reduction, such as palladium-carbon, Raney nickel, platinum oxide, platinum black, rhodium-aluminum oxide, triphenylphosphine-rhodium chloride or palladium-barium sulfate. The pressure for the reduction is not particularly limited, the reaction is carried out usually under from 1 to 10 atmospheres. The reaction temperature and reaction time can vary depending on the starting materials and the kind of catalyst employed, but the reaction is usually conducted at from 0° to 100° C. requiring from 5 minutes to 24 hours.

For an oxidative deprotection, the choice of solvent is not particularly limited provided that it does not participate in the reaction. The preferred solvent is an aqueous organic solvent, for which the organic solvent may be a ketone such as acetone; a halohydrocarbon such as methylene chloride, chloroform or carbon tetrachloride; a nitrile such as acetonitrile; an ether such as diethyl ether, tetrahydrofuran or dioxane; an amide such as dimethylformamide, dimethylacetamide or hexamethylphosphorotriamide; or a sulfoxide such as dimethylsulfoxide. The oxidizing agent is typically one employed for this kind of reaction and thus the choice is not particularly limited, being for example potassium persulfate, sodium persulfate, cerium ammonium nitrate (CAN) or 2,3-dichloro-5,6-dicyano-p-benzoquinone (DDQ). The reaction temperature and reaction time can vary depending on the starting materials and the kind of oxidizing reagent employed, but the reaction is generally performed at from 0° to 150° C. requiring from 10 minutes to 24 hours.

For deprotection using an alkali metal, the reaction is suitably performed with an alkali metal such as lithium metal or sodium metal in an alcohol such as methanol or ethanol, preferably at from −78° to −20° C.

For deprotection by treatment with a halide, suitable reagents include aluminum chloride-sodium iodide or an alkylsilyl halide such as trimethylsilyl iodide in a solvent. The choice of solvent is not particularly limited provided that it does not participate in the reaction. The preferred solvent is a nitrile such as acetonitrile; a halogenohydrocarbon such as methylene chloride or chloroform; or a mixed solvent thereof. The reaction temperature and reaction time can vary depending on the starting materials, but in general the reaction is conducted at from 0° to 50° C. requiring from 5 minutes to 3 days.

Where the amino protecting group is an alkenyloxycarbonyl group, it can generally be removed by treatment with a base under conditions similar to those already mentioned as appropriate for deprotection when the protecting group is an aliphatic acyl group, an aromatic acyl group, an alkoxycarbonyl group or a substituted methylene group forming a Schiff base Where the amino protecting group is an allyloxycarbonyl group, it can be easily removed with minimal side reactions by use of palladium together with triphenylcarbonyl or with nickel tetracarbonyl.

Depending on the choice of protecting groups and deprotection reaction conditions, it can be arranged that deprotection of a protected amino group also results at the same time in deprotection of a protected hydroxy group, as envisaged within optional conversion (3).

That part of optional conversion (3) where a hydroxy protecting group is removed, can be performed by customary methods which vary depending on the nature of the actual protecting group.

Where the hydroxy protecting group is a silyl group, an aralkyl group, an aralkyloxycarbonyl group, an aliphatic acyl group, an aromatic acyl group, or an alkoxycarbonyl group, or an alkenyloxycarbonyl group, it can be removed by the corresponding procedure given for removal of such a group when employed as an amino protecting group.

Where the hydroxy protecting group is an alkoxymethyl, tetrahydropyranyl, tetrahydrothiopyranyl, tetrahydrofuranyl or substituted ethyl group, it can be removed in general by treatment with an acid in a solvent. The acid, though not particularly limited, is preferably a Bronsted acid, an inorganic acid such as hydrochloric acid or sulfuric acid, an organic acid such as acetic acid or p-toluenesulfonic acid, or a strongly acidic cation exchange resin such as Dowex 50W. The choice of solvent is not particularly limited provided that it does not participate in the reaction, and is preferably an alcohol such as methanol or ethanol; an ether such as tetrahydrofuran or dioxane; or a mixed solvent thereof with water. The reaction temperature and reaction time can vary depending on the starting materials and the kind of acid employed, but the reaction is usually carried out at from 0° to 50° C. requiring from 10 minutes to 18 hours.

Where the hydroxy protecting group is an is employed for protection of the hydroxyl group, it can be removed according to the procedure when the amino-protecting group is an alkenyloxycarbonyl mentioned already.

Depending on the choice of protecting groups and deprotection reaction conditions, it can be arranged that deprotection of a protected hydroxy group also results at the same time in deprotection of a protected amino group, as envisaged in optional conversion (2) and within optional conversion (3).

After completion of the one or more optional conversions, the desired compound of general formula (I) of the present invention can be obtained from the reaction mixture by the use of conventional isolation methods. For example, a water-immiscible organic solvent is added to give a solvent extract which may be washed with water, and distilled to remove the solvent, thereby giving the target compound. If necessary, the target compound can be further purified by conventional techniques such as recrystallization, reprecipitation and/or chromatography.

The reactive carboxylic acid derivative of general formula (II) required as starting material for the process provided by the present invention can be prepared from the corresponding parent carboxylic acid, for example by conventional halogenation. Such halogenation is typically performed by treatment with a conventional halogenating agent. The halogenating agent is preferably a thionyl halide such as thionyl chloride, thionyl bromide or thionyl iodide; a sulfuryl halide such as sulfuryl chloride, sulfuryl bromide or sulfuryl iodide; a phosphorus trihalide such as phosphorus trichloride, phosphorus tribromide or phosphorus triiodide; a phosphorus pentahalide such as phosphorus pentachloride, phosphorus pentabromide or phosphorus pentaiodide; or a phosphorus oxyhalide such as phosphorus oxychloride, phosphorus oxybromide or phosphorus oxyiodide. A phosphorus oxyhalide is especially preferred as the halogenating agent.

The parent acid itself will be a known compound or one which can easily be prepared by known methods. A carboxylic acid such as 3-nitro-4-aminocinnamic acid having a nitro and an amino substituent can be synthesized, for example, according to the method described in Annalen Chimica 48, 958–991 (1958) or in Chem. Ber. 16, 2042. A carboxylic acid such as 3-nitro-4-hydroxycinnamic acid having a nitro and a hydroxy substituent can be synthesized, for example, according to the method described in J. Chem. Soc. 3072 (1952) or in J. Am. Chem. Soc. 79, 4114 (1957). A carboxylic acid having two amino substituents, or a carboxylic acid having an amino and a hydroxy substituent, can be prepared by reduction of a corresponding nitro compound.

Carboxylic acid compounds having more carbon atoms can be prepared by analogous methods or by methods relying on extension of the carbon chain. For example, a known aminocinnamic acid or hydroxycinnamic acid can be protected at the respective amino or hydroxy group, subjected to a carbon chain extension reaction, nitrated, and deprotected, followed optionally by reduction of the nitro substituent.

Various conventional reactions are available for increasing the number of carbons in the carboxylic acid. Typically, a starting carboxylic acid is reduced to the corresponding alcohol, then the hydroxy group is activated to form a leaving group such as a halogen atom, for example a chlorine, bromine or iodine atom; an alkanesulfonyloxy group, for example a methanesulfonyloxy or ethanesulfonyloxy group; a haloalkanesulfonyloxy group, for example a trifluoromethanesulfonyloxy or pentafluoroethanesulfonyloxy group; or an arylsulfonyloxy group, for example a benzenesulfonyloxy or p-toluenesulfonyloxy group, and then the carbon chain of the thereby activated compound is increased by one or two carbon atoms by adoption of one of the following procedures, usually effected at a temperature of from −78° C. to 50° C.).

As a method for increasing by one the carbon chain of the activated compound, there may be mentioned:

(1) use of 1,3-dicyan;

(2) use of a metal cyanide;

(3) reaction with carbon dioxide after preparation of a Grignard reagent.

As a method for increasing by two the carbon chain of the activated compound, there may be mentioned:

(1) use of a malonic acid derivative;

(2) acidolysis by use of an acetoacetic acid derivative.

The method using 1,3-dicyan can be performed by reaction of 1,3-dicyan with an organic or inorganic base, such as sodium hydride, potassium methoxide, potassium hydroxide or lithium diisopropylnitride, in an ether such as diethyl ether, diisopropyl ether, tetrahydrofuran or dioxane in an inert gas atmosphere such as nitrogen, to give its metal salt, which is then reacted with the activated compound, further followed by hydrolysis using a strong acid such as hydrochloric acid.

The method using a metal cyanide can be carried out by reaction of a metal cyanide with the activated compound to form the corresponding cyano compound followed by hydrolysis by conventional means.

The method by reaction with carbon dioxide after preparation of a Grignard reagent can be effected by preparing a Grignard reagent from the activated compound by conventional means followed by reaction with carbon dioxide in accordance with customary techniques.

The method by use of a malonic acid derivative can be carried out by reaction of a malonic acid derivative with a metal base in an ether such as diethyl ether, diisopropyl ether, tetrahydrofuran or dioxane to form the metal salt, followed by reaction with the activated compound by conventional means, further followed by decarbonation and/or hydrolysis. The choice of the metal base may depend on the pKa of the malonic acid derivative, but is suitably an inorganic base, for example an alkali metal carbonate such as sodium carbonate or potassium carbonate; an alkali metal hydride such as lithium hydride, sodium hydride or potassium hydride; or an alkali metal hydroxide such as sodium hydroxide, potassium hydroxide or barium hydroxide; an organic metal base like an alkali metal alkoxide such as sodium methoxide or sodium ethoxide; butyllithium; or lithium diisopropylamide.

The acidolytic method using an acetoacetic acid derivative can be performed by reaction of an acetoacetic acid derivative with a metal base such as one of those mentioned for the malonic acid method, in an ether such as diethyl ether, diisopropyl ether, tetrahydrofuran or dioxane, to form the metal salt at its methylene moiety, followed by reaction with the activated compound by conventional means, further followed by hydrolysis using an acid.

The Wittig reaction can also be used and represents a general method for increasing by any desired number of carbon atoms the length of the carbon chain of the carboxylic acid. When this method is employed, a carboxylic acid having a double bond at a desired position can be obtained, or alternatively the double bond can be removed by reduction. The Wittig reaction is suitably carried out by reaction of a Wittig reagent with an appropriate aldehyde, followed by the optional reduction of the double bond in the resultant product according to conventional procedures.

By a suitable combination of such reactions, a carboxylic acid of the desired chain length and desired degree of unsaturation can be synthesized.

Nitration of the carboxylic acid to introduce a nitro group is conveniently performed by conventional means. For example, it can be carried out by use of a nitrate derivative capable of introducing a nitro group, such as fuming nitric acid at from room temperature to 50° C. in an acid solvent such as acetic acid-acetic anhydride.

EXAMPLES OF THE INVENTION

The following Examples illustrate the preparation of compounds of the invention from known starting compounds or from starting compounds which may be prepared using procedures analogous to those employed for known compounds. Reference Examples are included for the preparation of some starting compounds. A Formulation Example is also given.

Example 1

N-(1-Adamantyl)-4-acetoxy-3-nitrocinnamamide 1 g of 4-acetoxy-3-nitrocinnamic acid (prepared as described in Preparation 2) was dissolved in 30 ml of methylene chloride. One drop of dimethylformamide was added to the resulting solution, and the mixture was cooled to 0° C. 3 g of oxalyl chloride were added to the mixture, which was then warmed to room temperature, after which it was stirred for 2 hours. At the end of this time, the solvent was completely removed by distillation under reduced pressure. The resulting residue was dissolved in 20 ml of methylene chloride, 0.6 g of 1-adamantylamine and 0.4 g of triethylamine were added, and the mixture was stirred for 3 hours. Ethyl acetate was then added to the solution, which was then washed with water, with a dilute aqueous solution of sodium hydrogencarbonate and with a saturated aqueous solution of sodium chloride, in that order. The organic layer was dried over anhydrous sodium sulfate, and the solvent was removed by distillation under reduced pressure. The resulting residue was purified by silica gel column chromatography, using 1:1 ethyl acetate:n-hexane as the eluent, to afford 1.2 g of the title compound, melting at 179°–180° C.

Example 2

N-(1-Adamantyl)-4-hydroxy-3-nitrocinnamamide 1 g of N-(1-adamantyl)-4-acetoxy-3-nitrocinnamamide (prepared as described in Example 1) was dissolved in 30 ml of methanol; 30 ml of a 4N aqueous solution of sodium hydroxide were then added, and the resulting mixture was stirred for 3 hours at room temperature. At the end of this time, the methanol was removed by distillation under reduced pressure. Addition of 3N aqueous hydrochloric acid to the residue afforded crystals of the title compound, melting at 162°–163° C.

Example 3

N-(1-Adamantyl)-3-(3-amino-4-hydroxyphenyl) propionamide

Crystals of N-(1-adamantyl)-4-hydroxy-3-nitrocinnamamide, prepared as described in Example 2, were collected by filtration and dissolved in 30 ml of methanol. 300 mg of 10% palladium-on-carbon were added to the solution, which was then reduced catalytically whilst bubbling hydrogen through it, under atmospheric pressure for 60 minutes. At the end of this time, the catalyst was filtered off, and the methanol was removed by distillation under reduced pressure. The resulting residue was purified by silica gel column chromatography, using ethyl acetate as the eluent, to afford 0.78 g of the title compound as crystals, melting at 79°–80° C.

Example 4

N,N-Diethyl-4-acetoxy-3-nitrocinnamamide

Following a procedure similar to that described in Example 1, but using 400 mg of diethylamine, 950 mg of the title compound were obtained as an oily substance.

Rf value: 0.85 (developed with ethyl acetate).

Example 5

N,N-Diethyl-4-hydroxy-3-nitrocinnamamide

Following a procedure similar to that described in Example 2, but using 900 mg of N,N-diethyl-4-acetoxy-3-nitrocinnamamide (prepared as described in Example 4), 750 mg of the title compound were obtained as an oily substance.

Rf value: 0.5 (developed with ethyl acetate:hexane, 1:1 by volume).

Example 6

N,N-Diethyl-3-(4-hydroxy-3-aminophenyl) propionamide

Following a procedure similar to that described in Example 3, but using 700 mg of N,N-diethyl-4-hydroxy-3-nitrocinnamamide (prepared as described in Example 5), 550 mg of the title compound were obtained, melting at 92°–93° C.

Example 7

N,N-Diphenyl-4-acetoxy-3-nitrocinnamamide

Following a procedure similar to that described in Example 1, but using 600 mg of diphenylamine, 1000 mg of the title compound were obtained, melting at 170.5°–171.5° C.

Example 8

N,N-Diphenyl-4-hydroxy-3-nitrocinnamamide

Following a procedure similar to that described in Example 2, but using 950 mg of N,N-diphenyl-4-acetoxy- 3-nitrocinnamamide (prepared as described in Example 7), 700 mg of the title compound were obtained, melting at 197°–198° C.

Example 9

N,N-Diphenyl-3-(4-hydroxy-3-aminophenyl)propionamide

Following a procedure similar to that described in Example 3, but using 650 mg of N,N-diphenyl-4-hydroxy-3-nitrocinnamamide (prepared as described in Example 8), 450 mg of the title compound were obtained, melting at 170.5°–171.5° C.

Example 10

N-[2-(3-Methoxycarbonyltetrahydrobenzothienyl)]-4-acetoxy-3-nitrocinnamamide

Following a procedure similar to that described in Example 1, but using 800 mg of 2-amino-3-methoxycarbonyltetrahydrobenzothiophene, 1000 mg of the title compound were obtained, melting at 184°–185° C.

Example 11

N-[2-(3-Methoxycarbonyltetrahydrobenzothienyl)]-4-hydroxy-3-nitrocinnamamide

Following a procedure similar to that described in Example 2, but using 950 mg of N-[2-(3-methoxycarbonyltetrahydrobenzothienyl)]-4-acetoxy-3-nitrocinnamamide (prepared as described in Example 10), 600 mg of the title compound were obtained, melting at 223°–224° C.

Example 12

N-(4-Benzyloxy-3-nitrocinnamoyl)piperidine

Following a procedure similar to that described in Example 1, but using 1 g of 4-benzyloxy-3-nitrocinnamic acid and 400 mg of piperidine, 0.8 g of the title compound were obtained, melting at 155°–156° C.

Example 13

N-[3-(4-Hydroxy-3-aminophenyl)propionyl]piperidine 0.5 g of N-(4-benzyloxy-3-nitrocinnamoyl)piperidine (prepared as described in Example 12) was dissolved in 30 ml of methanol. 300 mg of 10% palladium-on-carbon were added to the solution, which was then catalytically reduced whilst bubbling hydrogen through it, under atmospheric pressure for 60 minutes. The catalyst was then removed by filtration, and the methanol was removed by distillation under reduced pressure. The resulting residue was purified by silica gel column chromatography, using ethyl acetate as the eluent, to afford 0.35 g of the title compound as crystals, melting at 149°–150° C.

Example 14

N-Isobutyl-4-benzyloxy-3-nitrocinnamamide

Following a procedure similar to that described in Example 1, but using 400 mg of isobutylamine, 850 mg of the title compound were obtained, melting at 166°–167° C.

Example 15

N-Isobutyl-3-(4-hydroxy-3-aminophenyl)propionamide

Following a procedure similar to that described in Example 13, but using 800 mg of N-isobutyl-4-benzyloxy-3-nitrocinnamamide (prepared as described in Example 14), 600 mg of the title compound were obtained as an oily substance.

Rf value: 0.19 (developed with ethyl acetate).

Example 16

N-(2,4-Dichlorophenyl)-4-benzyloxy-3-nitrocinnamamide

Following a procedure similar to that described in Example 12, but using 600 mg of 2,4-dichloroaniline, 900 mg of the title compound were obtained, melting at 152°–153° C.

Example 17

N-(2,4-Dichlorophenyl)-3-(4-hydroxy-3-aminophenyl)propionamide

Following a procedure similar to that described in Example 13, but using 850 mg of N-(2,4-dichlorophenyl)-4-benzyloxy-3-nitrocinnamamide (prepared as described in Example 16), 650 mg of the title compound were obtained, melting at 130°–131° C.

Example 18

N-(2,5-Dimethylphenyl)-4-benzyloxy-3-nitrocinnamamide

Following a procedure similar to that described in Example 12, but using 600 mg of 2,5-dimethylaniline, 850 mg of the title compound were obtained as an oily substance.

Rf value: 0.90 (developed with ethyl acetate).

Example 19

N-(2,5-Dimethylphenyl)-3-(4-hydroxy-3-aminophenyl)propionamide

Following a procedure similar to that described in Example 13, but using 800 mg of N-(2,5-dimethylphenyl)-4-benzyloxy-3-nitrocinnamamide (prepared as described in Example 18), 600 mg of the title compound were obtained, melting at 162°–163° C.

Example 20

N-(1-Adamantyl)-3-(3-nitro-4-trifluoroacetamidophenyl)propionamide 1 g of 3-(3-nitro-4-trifluoroacetamidophenyl)propionic acid (prepared as described in Preparation 5) was dissolved in 30 ml of methylene chloride. One drop of dimethylformamide was added to the resulting solution, which was then cooled to 0° C. 3 g of oxalyl chloride were then added to the solution, and after the temperature had increased to ambient, the resulting mixture was stirred for 2 hours. The solvent was then completely removed by distillation under reduced pressure, and the residue was dissolved in 20 ml of methylene chloride. 0.6 g of 1-adamantylamine and 0.4 g of triethylamine were then added to the resulting solution, which was then stirred for 3 hours. At the end of this time, ethyl acetate was added to the solution, which was then washed with water, with a dilute aqueous solution of sodium hydrogencarbonate and with a saturated aqueous solution of sodium chloride, in that order. The organic layer was separated and dried over anhydrous sodium sulfate. The solvent was then removed by distillation under reduced pressure.

The resulting residue was purified by silica gel column chromatography, using ethyl acetate as the eluent, to afford 1.0 g of the title compound as an oily substance.

Rf value: 0.71 (developed with ethyl acetate).

Example 21

N-(1-Adamantyl)-3-(3-nitro-4-aminophenyl)propionamide 0.5 g of N-(1-Adamantyl)-3-(3-nitro-4-trifluoroacetamidophenyl)propionamide (prepared as described in Example 20) was dissolved in 10 ml of methanol. 10 ml of a 2N aqueous solution of sodium hydroxide were then added to the solution, which was then stirred for 3 hours at room temperature. At the end of this time, the methanol was removed by distillation under reduced pressure. Extraction of the residue with ethyl acetate afforded the title compound as an oily substance.

Rf value: 0.38 (developed with ethyl acetate:hexane, 1:1 by volume).

Example 22

N-(1-Adamantyl)-3-(3,4-diaminophenyl)propionamide 500 mg of N-(1-adamantyl)-3-(3-nitro-4-aminophenyl)propionamide (prepared as described in Example 21) was dissolved in 20 ml of methanol. 200 mg of 10% w/w palladium-on-carbon was added to the solution, which was then catalytically reduced whilst bubbling hydrogen through it, under atmospheric pressure for 120 minutes. The catalyst was then removed by filtration, and the methanol was removed by distillation under reduced pressure. The resulting residue was purified by silica gel column chromatography, using 19:1 ethyl acetate:methanol as the eluent, to afford 0.21 g of the title compound as crystals, melting at 151°–152° C.

Example 23

N-(2,4-Dichlorophenyl)-3-(3-nitro-4-trifluoroacetamidophenyl)propionamide

Following a procedure similar to that described in Example 20, but using 800 mg of 2,4-dichloroaniline, 800 mg of the title compound were obtained, melting at 193°–194° C.

Example 24

N-(2,4-Dichlorophenyl)-3-(3-nitro-4-aminophenyl)propionamide

Following a procedure similar to that described in Example 21, but using 700 mg of N-(2,4-dichlorophenyl)-3-(3-nitro-4-trifluoroacetamidophenyl)propionamide (prepared as described in Example 23), 350 mg of the title compound were obtained, melting at 164°–165° C.

Example 25

N-(2,4-Dichlorophenyl)-3-(3,4-diaminophenyl)propionamide

Following a procedure similar to that described in Example 22, but using 300 mg of N-(2,4-dichlorophenyl)-3-(3-nitro-4-aminophenyl)propionamide (prepared as described in Example 24), 150 mg of the title compound were obtained, melting at 149°–150° C.

Example 26

N-[3-(3-Nitro-4-trifluoroacetamidophenyl)propionyl]morpholine

Following a procedure similar to that described in Example 20, but using 400 mg of morpholine, 900 mg of the title compound were obtained as an oily substance.

Rf value: 0.50 (developed with ethyl acetate).

Example 27

N-[3-(3-Nitro-4-aminophenyl)propionyl]morpholine

Following a procedure similar to that described in Example 21, but using 800 mg of N-[3-(3-nitro-4-trifluoroacetamidophenyl)propionyl]morpholine (prepared as described in Example 26), 600 mg of the title compound were obtained as an oily substance.

Rf value: 0.50 (developed with ethyl acetate:hexane, 1:1 by volume).

Example 28

N-[3-(3,4-diaminophenyl)propionyl]morpholine

Following a procedure similar to that described in Example 22, but using 500 mg of N-[3-(3-nitro-4-aminophenyl)propionyl]morpholine (prepared as described in Example 27), 300 mg of the title compound were obtained as an oily substance.

Rf value: 0.37 (developed with ethyl acetate:methanol, 4:1 by volume).

Example 29

N,N-Diethyl-3-(3-nitro-4-trifluoroacetamidophenyl)propionamide

Following a procedure similar to that described in Example 20, but using 400 mg of diethylamine, 1000 mg of the title compound were obtained as an oily substance.

Rf value: 0.70 (developed with ethyl acetate).

Example 30

N,N-Diethyl-3-(3-nitro-4-aminophenyl)propionamide

Following a procedure similar to that described in Example 21, but using 900 mg of N,N-diethyl-3-(3-nitro-4-trifluoroacetamidophenyl)propionamide (prepared as described in Example 29), 600 mg of the title compound were obtained, melting at 98°–99° C.

Example 31

N,N-Diethyl-3-(3,4-Diaminophenyl)propionamide

Following a procedure similar to that described in Example 22, but using 550 mg of N,N-diethyl-3-(3-nitro-4-aminophenyl)propionamide (prepared as described in Example 30), 300 mg of the title compound were obtained as crystals.

Rf value: 0.53 (developed with ethyl acetate:methanol, 4:1 by volume).

Example 32

N-(3-Quinolyl)-3-(3-nitro-4-trifluoroacetamidophenyl)propionamide

Following a procedure similar to that described in Example 20, but using 700 mg of 3-aminoquinoline, 900 mg of the title compound were obtained as an oily substance.

Rf value: 0.50 (developed with ethyl acetate).

Example 33

N-(3-Quinolyl)-3-(3-nitro-4-aminophenyl) propionamide

Following a procedure similar to that described in Example 21, but using 850 mg of N-(3-quinolyl)-3-(3-nitro-4-trifluoroacetamidophenyl)propionamide (prepared as described in Example 32), 600 mg of the title compound were obtained, melting at 219.5°–220.5° C.

Example 34

N-(3-Quinolyl)-3-(3,4-diaminophenyl)propionamide

Following a procedure similar to that described in Example 22, but using 500 mg of N-(3-quinolyl)-3-(3-nitro-4-aminophenyl)propionamide (prepared as described in Example 33), 300 mg of the title compound were obtained as crystals.

Rf value: 0.42 (developed with ethyl acetate:methanol, 4:1 by volume).

Example 35

N-(2,5-Dimethylphenyl)-3-(3-nitro-4-trifluoroacetamidophenyl)propionamide

Following a procedure similar to that described in Example 20, but using 600 mg of 2,5-dimethylaniline, 900 mg of the title compound were obtained as an oily substance.

Rf value: 0.45 (developed with ethyl acetate:hexane, 1:1 by volume).

Example 36

N-(2,5-Dimethylphenyl)-(4-amino-3-nitrophenyl) propionamide

Following a procedure similar to that described in Example 21, but using 800 mg of N-(2,5-dimethylphenyl)-3-(3-nitro-4-trifluoroacetamidophenyl)propionamide (prepared as described in Example 35), 600 mg of the title compound were obtained, melting at 187°–188° C.

Example 37

N-(2,5-Dimethylphenyl)-(3,4-diaminophenyl) propionamide

Following a procedure similar to that described in Example 22, but using 500 mg of N-(2,5-dimethylphenyl)-(4-amino-3-nitrophenyl)propionamide (prepared as described in Example 36), 300 mg of the title compound were obtained, melting at 120°–121° C.

Example 38

N,N-Diphenyl-3-(3-nitro-4-trifluoroacetamidophenyl)propionamide

Following a procedure similar to that described in Example 20, but using 600 mg of diphenylamine, 950 mg of the title compound were obtained as an oily substance.

Rf value: 0.56 (developed with ethyl acetate:hexane, 1:1 by volume).

Example 39

N,N-Diphenyl-3-(4-amino-3-nitrophenyl) propionamide

Following a procedure similar to that described in Example 21, but using 900 mg of N,N-diphenyl-3-(3-nitro-4-trifluoroacetamidophenyl)propionamide (prepared as described in Example 38), 750 mg of the title compound were obtained, melting at 189°–190° C.

Example 40

N,N-Diphenyl-3-(3,4-diaminophenyl)propionamide

Following a procedure similar to that described in Example 22, but using 600 mg of N,N-diphenyl-3-(4-amino-3-nitrophenyl)propionamide (prepared as described in Example 39), 300 mg of the title compound were obtained, melting at 122°–123° C.

Example 41

N-(4-Benzoylphenyl)-3-(3-nitro-4-trifluoroacetamidophenyl)propionamide

Following a procedure similar to that described in Example 20, but using 800 mg of 4-benzoylaniline, 1.1 g of the title compound were obtained as an oily substance.

Rf value: 0.63 (developed with ethyl acetate:hexane, 3:2 by volume).

Example 42

N-(4-Benzoylphenyl)-3-(4-amino-3-nitrophenyl) propionamide

Following a procedure similar to that described in Example 21, but using 1.0 g of N-(4-benzoylphenyl)-3-(3-nitro-4-trifluoroacetamidophenyl)propionamide (prepared as described in Example 41), 800 mg of the title compound were obtained, melting at 72°–73° C.

Example 43

N-(4-Benzoylphenyl)-3-(3,4-diaminophenyl) propionamide

Following a procedure similar to that described in Example 22, but using 700 mg of N-(4-benzoylphenyl)-3-(4-amino-3-nitrophenyl)propionamide (prepared as described in Example 42), 500 mg of the title compound were obtained, melting at 156°–157° C.

Example 44

N-([3-(3-Nitro-4-trifluoroacetamidophenyl) propionyl]piperidine

Following a procedure similar to that described in Example 20, but using 400 mg of piperidine, 800 mg of the title compound were obtained, melting at 102°–103° C.

Example 45

N-[3-(4-Amino-3-nitrophenyl)propionyl]piperidine

Following a procedure similar to that described in Example 21, but using 700 mg of N-([3-(3-nitro-4-trifluoroacetamidophenyl)propionyl]piperidine (prepared as described in Example 44), 500 mg of the title compound were obtained, melting at 140°–141° C.

Example 46

N-[3-(3,4-Diaminophenyl)propionyl]piperidine

Following a procedure similar to that described in Example 22, but using 400 mg of N-[3-(4-amino-3- nitrophenyl)propionyl]piperidine (prepared as described in Example 45, 200 mg of the title compound were obtained as an oily substance.

Rf value: 0.37 (developed with ethyl acetate:methanol, 9:1 by volume).

Example 47

N-Methyl-N-phenyl-3-(3-nitro-4-trifluoroacetamidophenyl)propionamide

Following a procedure similar to that described in Example 20, but using 500 mg of N-methylaniline, 1.1 g of the title compound were obtained as an oily substance.

Rf value: 0.40 (developed with a 1:1 mixture of ethyl acetate and n-hexane).

Example 48

N-Methyl-N-phenyl-3-(4-amino-3-nitrophenyl)propionamide

Following a procedure similar to that described in Example 21, but using 900 mg of N-methyl-N-phenyl-3-(3-nitro-4-trifluoroacetamidophenyl)propionamide (prepared as described in Example 47), 700 mg of the title compound were obtained as an oily substance.

Rf value: 0.33 (developed with ethyl acetate:hexane, 1:1 by volume).

Example 49

N-Methyl-N-phenyl-3-(3,4-diaminophenyl)propionamide

Following a procedure similar to that described in Example 22, but using 600 mg of N-methyl-N-phenyl-3-(4-amino-3-nitrophenyl)propionamide (prepared as described in Example 48), 400 mg of the title compound were obtained as an oily substance.

Rf value: 0.47 (developed with ethyl acetate:methanol, 9:1 by volume).

Example 50

N-(3-Quinolyl)-3-(3,4-diaminophenyl)propionamide hydrochloride

To a solution of 1 g of N-(3-quinolyl)-3-(3,4-diaminophenyl)propionamide (prepared as described in Example 34) in 20 ml of methanol were added 5 ml of 4N hydrogen chloride in dioxane with ice-cooling, and the solvent was distilled off. The residue was recrystallized from a mixture of methanol and ether to afford 0.7 g of the desired compound, melting at 246°–247° C.

Example 51

N-(1-Indanyl)-4-acetoxy-3-nitrocinnamamide

Following a procedure similar to that described in Example 1, but using 600 mg of 1-indanylamine, 1.0 g of the title compound were obtained, melting at 177°–178° C.

Example 52

N-(1-Indanyl)-4-hydroxy-3-nitrocinnamamide

Following a procedure similar to that described in Example 2, but using 900 mg of N-(1-indanyl)-4-acetoxy-3-nitrocinnamamide (prepared as described in Example 51), 700 mg of the title compound were obtained, melting at 203°–205° C.

Example 53

N-(1-Indanyl)-3-(4-hydroxy-3-aminophenyl)propionamide

Following a procedure similar to that described in Example 3, but using 600 mg of N-(1-indanyl)-4-hydroxy-3-nitrocinnamamide (prepared as described in Example 52), 400 mg of the title compound were obtained, melting at 130°–131° C.

Example 54

N-(4-Acetoxy-3-nitrocinnamoyl)morpholine

Following a procedure similar to that described in Example 1, but using 400 mg of morpholine, 900 mg of the title compound were obtained as an oily substance.

Rf value: 0.24 (developed with ethyl acetate:hexane, 1:1 by volume).

Example 55

N-(4-Hydroxy-3-nitrocinnamoyl)morpholine

Following a procedure similar to that described in Example 2, but using 800 mg of N-(4-acetoxy-3-nitrocinnamoyl)morpholine (prepared as described in Example 54), 600 mg of the title compound were obtained as an oily substance.

Rf value: 0.24 (developed with ethyl acetate:hexane, 1:1 by volume).

Example 56

N-[3-(4-Hydroxy-3-aminophenyl)propionyl]morpholine

Following a procedure similar to that described in Example 3, but using 500 mg of N-(4-hydroxy-3-nitrocinnamoyl)morpholine (prepared as described in Example 55), 400 mg of the title compound were obtained as an oily substance.

Rf value: 0.27 (developed with ethyl acetate).

Preparation 1

4-Hydroxy-3-nitrocinnamic acid 16.7 g of 4-hydroxy-3-nitrobenzaldehyde and 33.5 g of methyl triphenylphosphoranilideneacetate were dissolved in 100 ml of methylene chloride, and the resulting solution was stirred for 2 hours at room temperature. At the end of this time, the solvent was removed by distillation under reduced pressure. 300 ml of methanol and 18 g of sodium hydroxide were then added to the residue thus obtained, and the solution was heated under reflux for 2 hours. The methanol was then removed by distillation under reduced pressure. The residue was mixed with one liter of water, and insoluble matter was filtered off. The filtrate was acidified by the addition of 3N aqueous hydrochloric acid, and the crystals which separated were collected by filtration, and were dissolved in 500 ml of tetrahydrofuran. The solution was mixed with active charcoal, heated under reflux for 5 minutes and filtered whilst being kept warm. The solution was condensed to about 100 ml by evaporation under reduced pressure, and allowed to stand at room temperature to obtain 15.0 g of the title compound as a yellow solid.

Preparation 2

4-Acetoxy-3-nitrocinnamic acid 10 g of 4-hydroxy-3-nitrocinnamic acid (prepared as described in Preparation 1) were dissolved in 30 ml of acetic anhydride. One drop of sulfuric acid was added to the solution, which was then stirred for 2 hours at room temperature. 50 ml of water were added the solution, and it was then stirred for a further 2 hours. At the end of this time, ethyl acetate was added, and the mixture was washed with water and with a saturated aqueous solution of sodium chloride, in that order, and then dried over anhydrous sodium sulfate. The solvent was removed by distillation under reduced pressure, and the residue was mixed with toluene; the remaining acetic acid was removed by azeotropic distillation to obtain 10.2 g of the title compound as crystals.

Preparation 3

Ethyl 4-acetoaminophenylpropionate 10 g of ethyl 4-nitrocinnamate were dissolved in 100 ml of acetic acid, and 1 g of 10% w/w palladium-on-carbon was added to the solution, which was then reduced catalytically whilst bubbling hydrogen through it, under atmospheric pressure for 60 minutes. The catalyst was then removed by filtration, and the acetic acid was removed by distillation under reduced pressure. The residue thus obtained was mixed with 50 ml of acetic anhydride, and the resulting solution was allowed to stand overnight at room temperature. At the end of this time, the solvent was removed by distillation under reduced pressure. Purification by silica gel column chromatography afforded 7.8 g of the title compound as crystals.

Preparation 4

3-(4-Amino-3-nitrophenyl)propionic acid 5 g of ethyl 4-acetoaminophenylpropionate (prepared as described in Preparation 3) were dissolved in 30 ml of acetic acid and 30 ml of acetic anhydride. 10 ml of fuming nitric acid (specific gravity: 1.5) were then added dropwise to the solution at 40° C., which required 1 hour. The reaction mixture was then dropped into 300 ml of ice water. The crystals which separated were collected by filtration, and, after the addition of 30 ml of concentrated hydrochloric acid and 30 ml of acetic acid, were heated under reflux for 8 hours. The solvent was then removed by distillation under reduced pressure. Purification by silica gel column chromatography, using ethyl acetate as the eluent, afforded 2.2 g of the title compound, as an oil.

The product had an $R_f$ value of 0.62 by thin layer chromatography on silica gel when eluted with ethyl acetate.

Preparation 5

3-(3-Nitro-4-trifluoroacetamidophenyl)propionic acid 2 g of 3-(4-amino-3-nitrophenyl)propionic acid (prepared as described in Preparation 4) were dissolved in 10 ml of trifluoroacetic anhydride,. The solution was then stirred for 2 hours at room temperature, after which it was mixed with ethyl acetate, washed with water, and with a saturated aqueous solution of sodium chloride and dried over anhydrous sodium sulfate. The solvent was removed by distillation under reduced pressure, the residue was mixed with toluene and the remaining trifluoroacetic acid was removed by azeotropic distillation, to obtain 1.5 g of the title compound as crystals.

FORMULATION

Capsule Preparation

Powders of the following ingredients were thoroughly mixed and passed through a 60 mesh sieve (Tyler standard):

| | |
|---|---|
| N-(1-Adamantyl)-3-(3-amino-4-hydroxyphenyl)propionamide (prepared as described in Example 3) | 25.0 mg |
| Lactose | 153.6 mg |
| Corn starch | 100.0 mg |
| Magnesium stearate | 1.4 mg |
| Total | 280.0 mg |

280 mg of the resulting powder was put into a No. 3 gelatin capsule to make capsules.

We claim:

1. A compound which is selected from the group consisting of:

N-(3-quinolyl)-3-(3,4-diaminophenyl)propionamide,

N-(5-quinolyl)-3-(3,4-diaminophenyl)propionamide,

N-(8-quinolyl)-3-(3,4-diaminophenyl)propionamide,

N-(3-quinolyl)-3-(3,4-diaminophenyl)propionamide hydrochloride,

N-(5-quinolyl)-3-(3,4-diaminophenyl)propionamide hydrochloride,

N-(8-quinolyl)-3-(3,4-diaminophenyl)propionamide hydrochloride salts thereof.

2. Pharmaceutical compositions which comprise a pharmaceutically effective amount of a compound of claim 1, or a pharmaceutically acceptable salt thereof, together with a pharmaceutically acceptable carrier.

3. The compounds of claim 1, wherein the compound is N-(3-quinolyl)-3-(3,4-diaminophenyl) propionamide.

4. The composition of claim 2, wherein the compound is N-(3-quinolyl)-3-(3,4-diaminophenyl) propionamide.

5. The compound of claim 1 which is selected from the group consisting of,

N-(3-quinolyl)-3-(3,4-diaminophenyl)propionamide,

N-(5-quinolyl)-3-(3,4-diaminophenyl)propionamide,

N-(8-quinolyl)-3-(3,4-diaminophenyl)propionamide;

and salts thereof.

6. The compounds of claim 1, wherein the compound is N-(5-quinolyl)-3-(3,4-diaminophenyl)propionamide.

7. The compounds of claim 1, wherein the compound is N-(8-quinolyl)-(3,4-diaminophenyl)propionamide.

8. The compounds of claim 1, wherein the compound is N-(3-quinolyl)-(3,4-diaminophenyl)propionamide hydrochloride.

9. The compounds of claim 1, wherein the compound is N-(5-quinolyl)-3-(3,4-diaminophenyl)propionamide hydrochloride.

10. The compounds of claim 1, wherein the compound is N-(8-quinolyl)-3-(3,4-diaminophenyl)propionamide hydrochloride.

11. A method of treating a patient suffering from dementia comprising administering to the patient a pharmaceutically effective amount of the compound of claim 1, wherein said compound is either alone, or in combination with a pharmaceutically acceptable carrier.

12. A method of treating a patient suffering from cerebral ischemia by administering to the patient a pharmaceutically effective amount of the compound of claim 1, wherein said compound is either alone, or in combination with a pharmaceutically acceptable carrier.

13. A method of treating a patient suffering from Alzheimer's disease by administering to the patient a pharmaceutically effective amount of the compound of claim 1, wherein said compound is either alone, or in combination with a pharmaceutically acceptable carrier.

* * * * *